(12) United States Patent
Stern et al.

(10) Patent No.: US 12,376,904 B1
(45) Date of Patent: Aug. 5, 2025

(54) DYNAMIC LASER STABILIZATION AND CALIBRATION SYSTEM

(71) Applicant: EXIMO MEDICAL LTD., Rehovot (IL)

(72) Inventors: Oren Meshulam Stern, Shilo (IL); Ilan Ben Oren, Modiin (IL); Yonatan Romm, Efrat (IL)

(73) Assignee: AngioDynamics, Inc., Latham, NY (US)

( * ) Notice: Subject to any disclaimer, the term of this patent is extended or adjusted under 35 U.S.C. 154(b) by 247 days.

(21) Appl. No.: 17/469,839

(22) Filed: Sep. 8, 2021

Related U.S. Application Data

(60) Provisional application No. 63/075,480, filed on Sep. 8, 2020.

(51) Int. Cl.
| | | |
|---|---|---|
| A61B 18/00 | (2006.01) | |
| A61B 18/20 | (2006.01) | |
| A61B 18/22 | (2006.01) | |
| A61B 18/24 | (2006.01) | |

(52) U.S. Cl.
CPC .... *A61B 18/24* (2013.01); *A61B 2018/00577* (2013.01); *A61B 2018/00702* (2013.01); *A61B 2018/00761* (2013.01); *A61B 2018/00767* (2013.01); *A61B 2018/20553* (2017.05); *A61B 2018/2272* (2013.01)

(58) Field of Classification Search
CPC .......... A61B 18/24; A61B 2018/00577; A61B 2018/00702; A61B 2018/00761; A61B 2018/00767; A61B 2018/20553; A61B 2018/2272
See application file for complete search history.

(56) References Cited

U.S. PATENT DOCUMENTS

| | | | |
|---|---|---|---|
| 1,706,161 | A | 3/1929 | Hollnagel |
| 2,699,770 | A | 1/1955 | Fourestier |
| 3,043,910 | A | 7/1962 | Hicks, Jr. |
| 3,051,035 | A | 8/1962 | Root |
| 3,051,166 | A | 8/1962 | Hrair |
| 3,068,742 | A | 12/1962 | Hicks, Jr. |

(Continued)

FOREIGN PATENT DOCUMENTS

| | | |
|---|---|---|
| CA | 1326800 | 2/1994 |
| CA | 3017252 C | 12/2019 |

(Continued)

OTHER PUBLICATIONS

Jansen, E. Duco et al., Excimer, Ho: YAG, and Q-switched Ho: YAG ablation of aorta: a comparison of temperatures and tissue damage in vitro, Applied Optics, vol. 32, No. 4, Feb. 1, 1993, 9 pages.

(Continued)

*Primary Examiner* — Jennifer Pitrak McDonald
*Assistant Examiner* — Megan T Fedorky
(74) *Attorney, Agent, or Firm* — Kevin P. Radigan, Esq.; Heslin Rothenberg Farley & Mesiti P.C.

(57) ABSTRACT

Described is a laser ablation system arranged to dynamically adjust power output to provide increased stability and reduced fluctuations of emitted energy. Additionally described are a test catheter and calibration procedure for calibrating the laser ablation system for to dynamically adjust power output during an ablation procedure.

20 Claims, 9 Drawing Sheets

(56) References Cited

U.S. PATENT DOCUMENTS

| | | |
|---|---|---|
| 3,423,581 A | 1/1969 | Baer |
| 3,455,625 A | 7/1969 | Brumley |
| 3,572,325 A | 3/1971 | Bazell |
| 3,605,750 A | 9/1971 | Sheridan |
| 3,622,743 A | 11/1971 | Muncheryan |
| 3,641,332 A | 2/1972 | Reick |
| 3,643,653 A | 2/1972 | Takahashi |
| 3,678,741 A | 7/1972 | Burley |
| 3,704,996 A | 12/1972 | Borner |
| 3,710,798 A | 1/1973 | Bredemeier |
| 3,726,272 A | 4/1973 | Mori |
| 3,756,688 A | 9/1973 | Hudson |
| 3,768,146 A | 10/1973 | Braun |
| 3,780,295 A | 12/1973 | Kapron |
| 3,790,791 A | 2/1974 | Anderson |
| 3,796,905 A | 3/1974 | Maeda |
| 3,802,440 A | 4/1974 | Ziegler |
| 3,808,549 A | 4/1974 | Maurer |
| 3,832,028 A | 8/1974 | Kapron |
| 3,834,391 A | 9/1974 | Block |
| 3,834,803 A | 9/1974 | Tsukada |
| 3,843,865 A | 10/1974 | Nath |
| 3,846,010 A | 11/1974 | Love |
| 3,849,947 A | 11/1974 | Bunkoczy |
| 3,858,577 A | 1/1975 | Bass |
| 3,861,781 A | 1/1975 | Hasegawa |
| 3,866,599 A | 2/1975 | Johnson |
| 3,874,783 A | 4/1975 | Cole |
| 3,880,452 A | 4/1975 | Fields |
| 3,906,221 A | 9/1975 | Mercier |
| 3,910,677 A | 10/1975 | Becker |
| 3,920,980 A | 11/1975 | Nath |
| 3,932,184 A | 1/1976 | Cohen |
| 3,972,585 A | 8/1976 | Dalgleish |
| 4,005,522 A | 2/1977 | Dalgleish |
| 4,008,948 A | 2/1977 | Dalgleish |
| 4,087,158 A | 5/1978 | Lewis |
| 4,148,554 A | 4/1979 | Magnusson |
| 4,191,446 A | 3/1980 | Arditty |
| 4,233,493 A | 11/1980 | Nath |
| 4,273,109 A | 6/1981 | Enderby |
| 4,273,127 A | 6/1981 | Auth |
| 4,313,431 A | 2/1982 | Frank |
| 4,380,365 A | 4/1983 | Gross |
| 4,449,535 A | 5/1984 | Renault |
| 4,564,011 A | 1/1986 | Goldman |
| 4,573,761 A | 3/1986 | McLachlan |
| 4,578,061 A | 3/1986 | Lemelson |
| 4,592,353 A | 6/1986 | Daikuzono |
| 4,641,912 A | 2/1987 | Goldenberg |
| 4,654,532 A | 3/1987 | Hirschfeld |
| 4,660,925 A | 4/1987 | McCaughan, Jr. |
| 4,662,368 A | 5/1987 | Hussein |
| 4,666,426 A | 5/1987 | Aigner |
| 4,671,273 A | 6/1987 | Lindsey |
| 4,672,961 A | 6/1987 | Davies |
| 4,693,244 A | 9/1987 | Daikuzono |
| 4,693,556 A | 9/1987 | McCaughan, Jr. |
| 4,695,697 A | 9/1987 | Kosa |
| 4,697,595 A | 10/1987 | Breyer |
| 4,707,134 A | 11/1987 | McLachlan |
| 4,729,763 A | 3/1988 | Henrie |
| 4,732,448 A | 3/1988 | Goldenberg |
| 4,736,743 A | 4/1988 | Daikuzono |
| 4,740,047 A | 4/1988 | Abe |
| 4,743,084 A | 5/1988 | Manning |
| 4,773,413 A | 9/1988 | Hussein |
| 4,800,876 A | 1/1989 | Fox |
| 4,802,650 A | 2/1989 | Stricker |
| 4,812,003 A | 3/1989 | Dambach |
| 4,816,670 A | 3/1989 | Kitamura |
| 4,817,601 A | 4/1989 | Roth |
| 4,830,460 A | 5/1989 | Goldenberg |
| 4,832,024 A | 5/1989 | Boussignac |
| 4,834,493 A | 5/1989 | Cahill |
| 4,844,062 A | 7/1989 | Wells |
| 4,862,887 A | 9/1989 | Weber |
| 4,889,129 A | 12/1989 | Dougherty |
| 4,919,508 A | 4/1990 | Grace |
| 4,955,882 A | 9/1990 | Hakky |
| 4,966,596 A | 10/1990 | Kuntz |
| 4,968,306 A | 11/1990 | Huss |
| 4,968,314 A | 11/1990 | Michaels |
| 4,975,925 A | 12/1990 | Derrickson |
| 4,979,797 A | 12/1990 | Nemeth |
| 4,979,939 A | 12/1990 | Shiber |
| 4,985,029 A | 1/1991 | Hoshino |
| 4,988,163 A | 1/1991 | Cohen |
| 4,993,412 A | 2/1991 | Murphy-Chutorian |
| 4,995,691 A | 2/1991 | Purcell, Jr. |
| 4,998,794 A | 3/1991 | Holzman |
| 5,011,254 A | 4/1991 | Edwards |
| 5,011,279 A | 4/1991 | Auweter |
| 5,016,964 A | 5/1991 | Donnelly |
| 5,026,366 A | 6/1991 | Leckrone |
| 5,029,588 A | 7/1991 | Yock |
| 5,030,201 A | 7/1991 | Palestrant |
| 5,037,180 A | 8/1991 | Stone |
| 5,037,421 A | 8/1991 | Boutacoff |
| 5,041,109 A | 8/1991 | Abela |
| 5,042,980 A | 8/1991 | Baker |
| 5,053,033 A | 10/1991 | Clarke |
| 5,060,557 A | 10/1991 | Dunn |
| 5,074,632 A | 12/1991 | Potter |
| 5,093,877 A | 3/1992 | Aita |
| 5,100,507 A | 3/1992 | Cholewa |
| 5,112,127 A | 5/1992 | Carrabba |
| 5,129,896 A | 7/1992 | Hasson |
| 5,135,531 A | 8/1992 | Shiber |
| 5,146,917 A | 9/1992 | Wagnieres |
| 5,147,353 A | 9/1992 | Everett |
| 5,147,354 A | 9/1992 | Boutacoff |
| 5,151,096 A | 9/1992 | Khoury |
| 5,152,744 A | 10/1992 | Krause |
| 5,154,708 A | 10/1992 | Long |
| 5,157,750 A | 10/1992 | Grace |
| 5,164,945 A | 11/1992 | Long |
| 5,166,756 A | 11/1992 | McGee |
| 5,188,632 A | 2/1993 | Goldenberg |
| 5,188,635 A | 2/1993 | Radtke |
| 5,190,536 A | 3/1993 | Wood |
| 5,193,526 A | 3/1993 | Daikuzono |
| 5,196,004 A | 3/1993 | Sinofsky |
| 5,196,005 A | 3/1993 | Doiron |
| 5,207,669 A | 5/1993 | Baker |
| 5,222,966 A | 6/1993 | Perkins |
| 5,250,045 A | 10/1993 | Bohley |
| 5,253,312 A | 10/1993 | Payne |
| 5,254,114 A | 10/1993 | Reed, Jr. |
| 5,263,951 A | 11/1993 | Spears |
| 5,263,952 A | 11/1993 | Grace |
| 5,267,979 A | 12/1993 | Appling |
| 5,267,993 A | 12/1993 | Grace |
| 5,267,995 A | 12/1993 | Doiron |
| 5,269,777 A | 12/1993 | Doiron |
| 5,275,622 A | 1/1994 | Lazarus |
| 5,290,275 A | 3/1994 | Kittrell |
| 5,292,311 A | 3/1994 | Cope |
| 5,292,320 A | 3/1994 | Brown |
| 5,293,872 A | 3/1994 | Alfano |
| 5,300,066 A | 4/1994 | Manoukian |
| 5,306,274 A | 4/1994 | Long |
| 5,312,396 A | 5/1994 | Feld |
| 5,312,399 A | 5/1994 | Hakky |
| 5,315,614 A | 5/1994 | Grace |
| 5,321,783 A | 6/1994 | Nielson |
| 5,330,465 A | 7/1994 | Doiron |
| 5,342,383 A | 8/1994 | Thomas |
| 5,343,543 A | 8/1994 | Novak, Jr. |
| 5,346,488 A | 9/1994 | Prince |
| 5,349,590 A | 9/1994 | Amirkhanian |
| 5,350,377 A | 9/1994 | Winston |
| 5,352,221 A | 10/1994 | Fumich |
| 5,354,294 A | 10/1994 | Chou |

(56) References Cited

U.S. PATENT DOCUMENTS

| | | |
|---|---|---|
| 5,360,416 A | 11/1994 | Ausherman |
| 5,370,649 A | 12/1994 | Gardetto |
| 5,377,683 A | 1/1995 | Barken |
| 5,383,199 A | 1/1995 | Laudenslager |
| 5,395,361 A | 3/1995 | Fox |
| 5,400,428 A | 3/1995 | Grace |
| 5,401,270 A | 3/1995 | Mueller |
| 5,402,508 A | 3/1995 | O'Rourke |
| 5,404,218 A | 4/1995 | Nave |
| 5,415,633 A | 5/1995 | Lazarus |
| 5,415,653 A | 5/1995 | Wardle |
| 5,415,655 A | 5/1995 | Fuller |
| 5,419,312 A | 5/1995 | Arenberg |
| 5,421,928 A | 6/1995 | Knecht |
| 5,423,806 A | 6/1995 | Dale |
| 5,425,723 A | 6/1995 | Wang |
| 5,428,699 A | 6/1995 | Pon |
| 5,429,604 A | 7/1995 | Hammersmark |
| 5,429,617 A | 7/1995 | Hammersmark |
| 5,432,880 A | 7/1995 | Diner |
| 5,445,608 A | 8/1995 | Chen |
| 5,456,680 A | 10/1995 | Taylor |
| 5,464,395 A | 11/1995 | Faxon |
| 5,466,234 A | 11/1995 | Loeb |
| 5,470,330 A | 11/1995 | Goldenberg |
| 5,484,433 A | 1/1996 | Taylor |
| 5,486,170 A | 1/1996 | Winston |
| 5,495,541 A | 2/1996 | Murray |
| 5,498,258 A | 3/1996 | Hakky |
| 5,499,975 A | 3/1996 | Cope |
| 5,509,917 A | 4/1996 | Cecchetti |
| 5,514,128 A | 5/1996 | Hillsman |
| 5,534,000 A | 7/1996 | Bruce |
| 5,536,248 A | 7/1996 | Weaver |
| 5,536,265 A | 7/1996 | Van Den Bergh |
| 5,562,657 A | 10/1996 | Griffin |
| 5,571,098 A | 11/1996 | Domankevitz |
| 5,624,026 A | 4/1997 | Chernoff |
| 5,631,986 A | 5/1997 | Frey |
| 5,643,251 A | 7/1997 | Hillsman |
| 5,643,253 A | 7/1997 | Baxter |
| 5,643,257 A | 7/1997 | Cohen |
| 5,653,696 A | 8/1997 | Shiber |
| 5,662,646 A | 9/1997 | Fumich |
| 5,688,263 A | 11/1997 | Hauptmann |
| 5,693,029 A | 12/1997 | Leonhardt |
| 5,693,043 A | 12/1997 | Kittrell |
| 5,695,482 A | 12/1997 | Kaldany |
| 5,695,583 A | 12/1997 | Van Den Bergh |
| 5,700,243 A | 12/1997 | Narciso, Jr. |
| 5,710,626 A | 1/1998 | O'Rourke |
| 5,717,807 A | 2/1998 | Theroux |
| 5,720,894 A | 2/1998 | Perry |
| 5,725,521 A | 3/1998 | Mueller |
| 5,728,091 A | 3/1998 | Payne |
| 5,754,717 A | 5/1998 | Esch |
| 5,764,840 A | 6/1998 | Wach |
| 5,769,868 A | 6/1998 | Yock |
| 5,782,797 A | 7/1998 | Schweich, Jr. |
| 5,807,389 A | 9/1998 | Gardetto |
| 5,810,662 A | 9/1998 | Van Becelaere |
| 5,817,144 A | 10/1998 | Gregory |
| 5,836,940 A | 11/1998 | Gregory |
| 5,836,946 A | 11/1998 | Diaz |
| 5,843,073 A | 12/1998 | Sinofsky |
| 5,868,734 A | 2/1999 | Soufiane |
| 5,878,178 A | 3/1999 | Wach |
| 5,897,551 A | 4/1999 | Everett |
| 5,908,415 A | 6/1999 | Sinofsky |
| 5,916,210 A | 6/1999 | Winston |
| 5,947,959 A | 9/1999 | Sinofsky |
| 5,951,482 A | 9/1999 | Winston |
| 5,951,543 A | 9/1999 | Brauer |
| 5,976,124 A | 11/1999 | Reiser |
| 5,989,243 A | 11/1999 | Goldenberg |
| 5,991,404 A | 11/1999 | Brahami |
| 6,013,072 A | 1/2000 | Winston et al. |
| 6,027,450 A | 2/2000 | Brown |
| 6,033,398 A | 3/2000 | Farley |
| 6,048,349 A | 4/2000 | Winston |
| 6,053,809 A | 4/2000 | Arceneaux |
| 6,056,743 A | 5/2000 | Ellis |
| 6,063,093 A | 5/2000 | Winston |
| 6,096,011 A | 8/2000 | Trombley, III |
| 6,102,905 A | 8/2000 | Baxter |
| 6,106,515 A | 8/2000 | Winston |
| 6,117,125 A | 9/2000 | Rothbarth |
| 6,126,654 A | 10/2000 | Giba |
| 6,139,543 A | 10/2000 | Esch |
| 6,152,919 A | 11/2000 | Hakky |
| 6,162,214 A | 12/2000 | Mueller |
| 6,164,280 A | 12/2000 | Everett |
| 6,179,808 B1 | 1/2001 | Boukhny |
| 6,193,676 B1 | 2/2001 | Winston |
| 6,206,898 B1 | 3/2001 | Honeycutt |
| 6,210,400 B1 | 4/2001 | Hebert |
| 6,228,076 B1 | 5/2001 | Winston |
| 6,251,100 B1 | 6/2001 | Flock |
| 6,258,084 B1 | 7/2001 | Goldman |
| 6,263,236 B1 | 7/2001 | Kasinkas |
| 6,270,492 B1 | 8/2001 | Sinofsky |
| 6,270,495 B1 | 8/2001 | Palermo |
| 6,283,951 B1 | 9/2001 | Flaherty |
| 6,302,875 B1 | 10/2001 | Makower |
| 6,344,048 B1 | 2/2002 | Chin |
| 6,352,549 B1 | 3/2002 | Everett |
| 6,375,651 B2 | 4/2002 | Grasso, III |
| 6,394,976 B1 | 5/2002 | Winston |
| 6,398,777 B1 | 6/2002 | Navarro |
| 6,439,944 B1 | 8/2002 | La Fata |
| 6,440,125 B1 | 8/2002 | Rentrop |
| 6,447,477 B2 | 9/2002 | Burney |
| 6,451,010 B1 | 9/2002 | Angeley |
| 6,454,790 B1 | 9/2002 | Neuberger |
| 6,463,313 B1 | 10/2002 | Winston |
| 6,485,485 B1 | 11/2002 | Winston |
| 6,514,217 B1 | 2/2003 | Selmon |
| 6,522,806 B1 | 2/2003 | James, IV |
| 6,539,944 B1 | 4/2003 | Watson |
| 6,544,230 B1 | 4/2003 | Flaherty |
| 6,547,757 B1 | 4/2003 | Kranz |
| 6,547,779 B2 | 4/2003 | Levine |
| 6,551,302 B1 | 4/2003 | Rosinko |
| 6,554,824 B2 | 4/2003 | Davenport |
| 6,555,827 B1 | 4/2003 | Kockott |
| 6,561,998 B1 | 5/2003 | Roth |
| 6,599,277 B2 | 7/2003 | Neubert |
| 6,611,720 B2 | 8/2003 | Hata |
| 6,628,519 B2 | 9/2003 | Umetsu |
| 6,652,803 B2 | 11/2003 | Watanabe |
| 6,663,621 B1 | 12/2003 | Winston |
| 6,673,064 B1 | 1/2004 | Rentrop |
| 6,673,065 B1 | 1/2004 | Veligdan |
| 6,685,648 B2 | 2/2004 | Flaherty |
| 6,692,466 B1 | 2/2004 | Chow |
| 6,701,044 B2 | 3/2004 | Arbore |
| 6,716,210 B2 | 4/2004 | Lin |
| 6,746,422 B1 | 6/2004 | Noriega |
| 6,752,800 B1 | 6/2004 | Winston |
| 6,752,803 B2 | 6/2004 | Goldman |
| 6,767,338 B2 | 7/2004 | Hawk |
| 6,769,433 B2 | 8/2004 | Zikorus |
| 6,772,014 B2 | 8/2004 | Coe |
| 6,775,447 B2 | 8/2004 | Nicholson |
| 6,796,710 B2 | 9/2004 | Yates |
| 6,842,639 B1 | 1/2005 | Winston |
| 6,845,193 B2 | 1/2005 | Loeb |
| 6,852,109 B2 | 2/2005 | Winston |
| 6,926,692 B2 | 8/2005 | Katoh |
| 6,951,554 B2 | 10/2005 | Johansen |
| 6,962,584 B1 | 11/2005 | Stone |
| 6,962,585 B2 | 11/2005 | Poleo, Jr. |
| 6,967,767 B2 | 11/2005 | Nicholson |
| 6,970,732 B2 | 11/2005 | Winston |

(56) References Cited

U.S. PATENT DOCUMENTS

| | | |
|---|---|---|
| 6,978,783 B2 | 12/2005 | Svendsen |
| 6,986,764 B2 | 1/2006 | Davenport |
| 6,986,766 B2 | 1/2006 | Caldera |
| 6,989,004 B2 | 1/2006 | Hinchliffe |
| 7,050,692 B2 | 5/2006 | Harlan |
| 7,059,330 B1 | 6/2006 | Makower |
| 7,063,610 B2 | 6/2006 | Mysker |
| 7,063,695 B2 | 6/2006 | Nield |
| 7,128,735 B2 | 10/2006 | Weston |
| 7,141,041 B2 | 11/2006 | Seward |
| 7,163,535 B2 | 1/2007 | Ryba |
| 7,167,622 B2 | 1/2007 | Temelkuran |
| 7,172,576 B2 | 2/2007 | Sawa |
| 7,186,252 B2 | 3/2007 | Nobis |
| 7,247,162 B1 | 7/2007 | Thornton |
| 7,257,302 B2 | 8/2007 | Fermann |
| 7,267,674 B2 | 9/2007 | Brucker |
| 7,273,469 B1 | 9/2007 | Chan |
| 7,273,478 B2 | 9/2007 | Appling |
| 7,284,981 B2 | 10/2007 | Schmid |
| 7,288,087 B2 | 10/2007 | Winston |
| 7,303,533 B2 | 12/2007 | Johansen |
| 7,331,954 B2 | 2/2008 | Temelkuran |
| 7,357,797 B2 | 4/2008 | Ryba |
| 7,377,910 B2 | 5/2008 | Katoh |
| 7,379,648 B1 | 5/2008 | Brooks |
| 7,381,200 B2 | 6/2008 | Katoh |
| 7,391,561 B2 | 6/2008 | Di Teodoro |
| 7,412,132 B1 | 8/2008 | Liu |
| 7,430,352 B2 | 9/2008 | Di Teodoro |
| 7,450,618 B2 | 11/2008 | Dantus |
| 7,458,967 B2 | 12/2008 | Appling |
| 7,479,147 B2 | 1/2009 | Honeycutt |
| 7,483,204 B2 | 1/2009 | Harter |
| 7,499,756 B2 | 3/2009 | Bowe |
| 7,503,914 B2 | 3/2009 | Coleman |
| 7,513,886 B2 | 4/2009 | Konstantino |
| 7,519,253 B2 | 4/2009 | Islam |
| 7,524,289 B2 | 4/2009 | Lenker |
| 7,524,316 B2 | 4/2009 | Hennings |
| 7,559,329 B2 | 7/2009 | Appling |
| 7,563,262 B2 | 7/2009 | Winston |
| 7,567,596 B2 | 7/2009 | Dantus |
| 7,572,254 B2 | 8/2009 | Hebert |
| 7,644,715 B2 | 1/2010 | Hayes |
| 7,651,503 B1 | 1/2010 | Coe |
| 7,666,161 B2 | 2/2010 | Nash |
| 7,699,790 B2 | 4/2010 | Simpson |
| 7,724,787 B2 | 5/2010 | Murison et al. |
| 7,779,842 B1 | 8/2010 | Russo |
| 7,787,506 B1 | 8/2010 | Jiang |
| 7,809,222 B2 | 10/2010 | Hartl |
| 7,811,281 B1 | 10/2010 | Rentrop |
| 7,828,793 B2 | 11/2010 | Thompson |
| 7,834,331 B2 | 11/2010 | Ben-Yakar |
| 7,837,677 B2 | 11/2010 | Thompson |
| 7,837,678 B2 | 11/2010 | Thompson |
| 7,846,153 B2 | 12/2010 | Hebert |
| 7,879,011 B2 | 2/2011 | Chang |
| D634,007 S | 3/2011 | Zinger |
| 7,912,554 B2 | 3/2011 | Capuano |
| 7,921,854 B2 | 4/2011 | Hennings |
| 7,924,892 B2 | 4/2011 | Chuang |
| 7,927,784 B2 | 4/2011 | Simpson |
| 7,929,579 B2 | 4/2011 | Hohm |
| 7,931,659 B2 | 4/2011 | Bose |
| 7,942,852 B2 | 5/2011 | Mas |
| 7,951,094 B2 | 5/2011 | Johansen |
| 7,957,790 B2 | 6/2011 | Kleen |
| 7,959,608 B2 | 6/2011 | Nash |
| 7,963,947 B2 | 6/2011 | Kurth |
| 7,963,961 B2 | 6/2011 | Thompson |
| 7,963,962 B2 | 6/2011 | Thompson |
| 7,975,528 B2 | 7/2011 | Hart |
| 7,976,533 B2 | 7/2011 | Larsson |
| 7,993,359 B1 | 8/2011 | Atwell |
| 8,016,784 B1 | 9/2011 | Hayzelden |
| 8,043,285 B2 | 10/2011 | Thompson |
| 8,059,274 B2 | 11/2011 | Splinter |
| 8,062,226 B2 | 11/2011 | Moore |
| 8,073,019 B2 | 12/2011 | Liu |
| 8,097,012 B2 | 1/2012 | Kagarise |
| 8,100,893 B2 | 1/2012 | Dadisman |
| 8,104,483 B2 | 1/2012 | Taylor |
| 8,114,429 B2 | 2/2012 | Michal |
| 8,128,951 B2 | 3/2012 | Michal |
| 8,157,747 B2 | 4/2012 | Grata |
| 8,182,474 B2 | 5/2012 | Winston |
| 8,189,971 B1 | 5/2012 | Vaissie |
| 8,202,268 B1 | 6/2012 | Wells |
| 8,238,386 B2 | 8/2012 | Limpert |
| 8,246,580 B2 | 8/2012 | Hopkins |
| 8,257,722 B2 | 9/2012 | Michal |
| 8,291,915 B2 | 10/2012 | Farley |
| 8,298,215 B2 | 10/2012 | Zinn |
| 8,300,669 B2 | 10/2012 | Dantus |
| 8,317,779 B2 | 11/2012 | Mirkov |
| 8,321,019 B2 | 11/2012 | Esch |
| 8,348,844 B2 | 1/2013 | Kunjan |
| 8,350,183 B2 | 1/2013 | Vogel |
| 8,353,899 B1 | 1/2013 | Wells |
| 8,365,741 B2 | 2/2013 | Hennings |
| 8,366,735 B2 | 2/2013 | Bose |
| 8,413,664 B2 | 4/2013 | Appling |
| 8,414,568 B2 | 4/2013 | Harlan |
| 8,422,134 B2 | 4/2013 | Wu |
| 8,425,501 B2 | 4/2013 | Appling |
| 8,428,747 B2 | 4/2013 | Coe |
| 8,435,235 B2 | 5/2013 | Stevens |
| 8,439,874 B2 | 5/2013 | Hertweck |
| 8,460,312 B2 | 6/2013 | Bose |
| 8,465,467 B2 | 6/2013 | Gao |
| 8,465,480 B2 | 6/2013 | Winston |
| 8,470,010 B2 | 6/2013 | Jakubowski |
| 8,486,051 B2 | 7/2013 | Larsson |
| 8,491,925 B2 | 7/2013 | Michal |
| 8,500,697 B2 | 8/2013 | Kurth |
| 8,512,326 B2 | 8/2013 | Shadduck |
| 8,535,360 B2 | 9/2013 | O'Dowd |
| 8,545,432 B2 | 10/2013 | Renati |
| 8,545,468 B2 | 10/2013 | Fabo |
| 8,551,067 B2 | 10/2013 | Zinger |
| 8,563,023 B2 | 10/2013 | Michal |
| 8,587,864 B2 | 11/2013 | Harter |
| 8,636,726 B1 | 1/2014 | Wells |
| 8,636,729 B2 | 1/2014 | Esch |
| 8,657,785 B2 | 2/2014 | Torrance |
| 8,668,665 B2 | 3/2014 | Gerg |
| 8,673,332 B2 | 3/2014 | Michal |
| 8,684,953 B2 | 4/2014 | Cabiri |
| 8,684,994 B2 | 4/2014 | Lev |
| 8,696,695 B2 | 4/2014 | Patel |
| 8,702,773 B2 | 4/2014 | Keeler |
| 8,721,634 B2 | 5/2014 | Esch |
| 8,728,066 B2 | 5/2014 | Shadduck |
| 8,734,825 B2 | 5/2014 | Michal |
| 8,752,598 B2 | 6/2014 | Denenburg |
| 8,753,325 B2 | 6/2014 | Lev |
| 8,758,333 B2 | 6/2014 | Harlan |
| 8,767,287 B2 | 7/2014 | Clowes |
| 8,784,394 B2 | 7/2014 | Kerr |
| 8,808,074 B2 | 8/2014 | Kim |
| 8,814,922 B2 | 8/2014 | Hennings |
| 8,840,606 B2 | 9/2014 | Appling |
| 8,852,145 B2 | 10/2014 | Denenburg |
| 8,852,165 B2 | 10/2014 | MacKay, II |
| 8,852,178 B2 | 10/2014 | Thompson |
| 8,855,151 B2 | 10/2014 | Harter |
| 8,861,075 B2 | 10/2014 | Dantus |
| 8,864,754 B2 | 10/2014 | Appling |
| 8,864,755 B2 | 10/2014 | Appling |
| 8,881,735 B2 | 11/2014 | Mitchell |
| 8,887,733 B2 | 11/2014 | Appling |
| D720,451 S | 12/2014 | Denenburg |

(56) References Cited

U.S. PATENT DOCUMENTS

| | | |
|---|---|---|
| 8,905,994 B1 | 12/2014 | Lev |
| 8,915,896 B2 | 12/2014 | Sanders |
| 8,920,402 B2 | 12/2014 | Nash |
| 8,953,648 B2 | 2/2015 | Ishaaya |
| 8,956,376 B2 | 2/2015 | Alvarez |
| 8,961,551 B2 | 2/2015 | Taylor |
| 8,979,792 B2 | 3/2015 | Lev |
| 8,979,828 B2 | 3/2015 | Fix |
| 8,998,875 B2 | 4/2015 | Lev |
| 8,998,936 B2 | 4/2015 | Alvarez |
| 9,028,520 B2 | 5/2015 | Taylor |
| 9,034,362 B2 | 5/2015 | Michal |
| 9,044,829 B2 | 6/2015 | Crist |
| 9,050,127 B2 | 6/2015 | Bonnette |
| 9,066,736 B2 | 6/2015 | Islam |
| 9,066,742 B2 | 6/2015 | Splinter |
| D734,868 S | 7/2015 | Gilboa |
| 9,119,656 B2 | 9/2015 | Bose |
| 9,119,907 B2 | 9/2015 | Sherman |
| 9,125,562 B2 | 9/2015 | Spencer |
| 9,132,211 B2 | 9/2015 | Michal |
| D740,946 S | 10/2015 | Szabo |
| 9,162,038 B2 | 10/2015 | Rottenberg |
| D742,520 S | 11/2015 | Szabo |
| D742,521 S | 11/2015 | Szabo |
| D742,522 S | 11/2015 | Szabo |
| 9,198,968 B2 | 12/2015 | Michal |
| 9,199,011 B2 | 12/2015 | Locke |
| 9,216,056 B2 | 12/2015 | Datta |
| 9,220,523 B2 | 12/2015 | Taylor |
| D748,266 S | 1/2016 | Szabo |
| 9,238,122 B2 | 1/2016 | Malhi |
| 9,248,221 B2 | 2/2016 | Look |
| 9,254,175 B2 | 2/2016 | Winston |
| 9,283,039 B2 | 3/2016 | Harlan |
| 9,283,040 B2 | 3/2016 | Hendrick |
| 9,287,677 B2 | 3/2016 | Clowes |
| 9,289,173 B2 | 3/2016 | Splinter |
| 9,289,226 B2 | 3/2016 | Taylor |
| 9,291,663 B2 | 3/2016 | Grace |
| 9,295,373 B2 | 3/2016 | Torrance |
| D753,289 S | 4/2016 | Shimon |
| D753,290 S | 4/2016 | Shimon |
| 9,308,047 B2 | 4/2016 | Taylor |
| 9,320,530 B2 | 4/2016 | Grace |
| 9,333,007 B2 | 5/2016 | Escudero |
| 9,339,337 B2 | 5/2016 | Fix |
| 9,345,508 B2 | 5/2016 | Hendrick |
| 9,345,510 B2 | 5/2016 | Patel |
| 9,358,042 B2 | 6/2016 | Magee |
| 9,368,931 B2 | 6/2016 | Bragagna |
| 9,408,665 B2 | 8/2016 | Sauro |
| 9,408,998 B2 | 8/2016 | Alvarez |
| 9,413,896 B2 | 8/2016 | Bowe |
| 9,421,035 B2 | 8/2016 | Hendrick |
| 9,421,065 B2 | 8/2016 | Splinter |
| 9,456,672 B2 | 10/2016 | Condon |
| 9,456,872 B2 | 10/2016 | Hendrick |
| 9,510,854 B2 | 12/2016 | Mallaby |
| D775,728 S | 1/2017 | Cavada et al. |
| 9,566,116 B2 | 2/2017 | Winston |
| 9,603,618 B2 | 3/2017 | Grace |
| 9,622,819 B2 | 4/2017 | Mitchell |
| 9,623,211 B2 | 4/2017 | Hendrick |
| 9,636,482 B2 | 5/2017 | McDaniel |
| 9,642,646 B2 | 5/2017 | Patel |
| 9,649,158 B2 | 5/2017 | Datta |
| 9,649,159 B2 | 5/2017 | Keeler |
| 9,655,633 B2 | 5/2017 | Leynov |
| 9,662,478 B2 | 5/2017 | Browd |
| 9,668,765 B2 | 6/2017 | Grace |
| 9,668,766 B2 | 6/2017 | Rottenberg |
| 9,675,371 B2 | 6/2017 | Shimon |
| 9,675,415 B2 | 6/2017 | Varghese |
| 9,676,167 B2 | 6/2017 | Marjanovic |
| 9,678,405 B2 | 6/2017 | Mironov |
| 9,681,882 B2 | 6/2017 | Garrison |
| 9,694,118 B2 | 7/2017 | Esnouf |
| 9,724,122 B2 | 8/2017 | Hendrick |
| 9,730,756 B2 | 8/2017 | Ben Oren |
| 9,731,098 B2 | 8/2017 | Hendrick |
| 9,731,113 B2 | 8/2017 | Grace |
| 9,757,200 B2 | 9/2017 | Magee et al. |
| 9,760,518 B2 | 9/2017 | Grossman |
| 9,763,692 B2 | 9/2017 | Bowe |
| 9,770,536 B2 | 9/2017 | Speck |
| 9,774,161 B2 | 9/2017 | Zach |
| 9,775,969 B2 | 10/2017 | Alvarez |
| 9,795,505 B2 | 10/2017 | Yu |
| 9,801,650 B2 | 10/2017 | Taylor |
| 9,803,973 B1 | 10/2017 | Sajedi |
| 9,808,275 B2 | 11/2017 | Taylor |
| 9,808,277 B2 | 11/2017 | Nash |
| 9,814,862 B2 | 11/2017 | Alvarez |
| 9,820,761 B2 | 11/2017 | Garrison |
| 9,821,090 B2 | 11/2017 | Triffo |
| 9,827,055 B2 | 11/2017 | Hendrick |
| 9,844,410 B2 | 12/2017 | Mitchell |
| 9,844,485 B2 | 12/2017 | Locke |
| 9,848,952 B2 | 12/2017 | Khanna |
| 9,855,100 B2 | 1/2018 | Splinter |
| 9,855,374 B2 | 1/2018 | Sherman |
| 9,864,140 B2 | 1/2018 | Adler |
| 9,878,399 B2 | 1/2018 | Liu |
| 9,882,342 B2 | 1/2018 | Zach |
| 9,883,877 B2 | 2/2018 | Look |
| 9,883,885 B2 | 2/2018 | Hendrick |
| 9,884,184 B2 | 2/2018 | Triffo |
| 9,895,473 B2 | 2/2018 | Look |
| 9,907,614 B2 | 3/2018 | Grace |
| 9,907,615 B2 | 3/2018 | Keeler |
| 9,913,688 B1 | 3/2018 | Karavitis |
| 9,918,729 B2 | 3/2018 | Taylor |
| 9,925,316 B2 | 3/2018 | Sanders |
| 9,925,366 B2 | 3/2018 | Grace |
| 9,925,371 B2 | 3/2018 | Grace |
| 9,931,166 B2 | 4/2018 | Sauro |
| 9,937,005 B2 | 4/2018 | Hendrick |
| 9,949,753 B2 | 4/2018 | Bowe |
| 9,958,385 B2 | 5/2018 | Manassen |
| 9,962,527 B2 | 5/2018 | Laudenslager |
| 9,980,743 B2 | 5/2018 | Grace |
| 9,999,468 B2 | 6/2018 | Chalfant |
| 10,010,657 B2 | 7/2018 | Torrance |
| 10,039,569 B2 | 8/2018 | Hendrick |
| 10,046,093 B2 | 8/2018 | Michal |
| 10,052,129 B2 | 8/2018 | Grace |
| 10,079,466 B2 | 9/2018 | Ishaaya |
| 10,080,608 B2 | 9/2018 | Datta |
| 10,085,883 B2 | 10/2018 | Auld |
| 10,092,357 B2 | 10/2018 | Fix |
| 10,092,363 B2 | 10/2018 | Magee |
| 10,105,533 B2 | 10/2018 | Grace |
| 10,111,709 B2 | 10/2018 | Taylor |
| 10,117,970 B2 | 11/2018 | Michal |
| 10,135,225 B2 | 11/2018 | Weichmann |
| 10,136,913 B2 | 11/2018 | Grace |
| 10,141,709 B2 | 11/2018 | Ishaaya |
| 10,149,718 B2 | 12/2018 | Fiser |
| 10,166,375 B2 | 1/2019 | Browd |
| 10,183,150 B2 | 1/2019 | McDaniel |
| 10,183,151 B2 | 1/2019 | Alvarez |
| 10,201,315 B2 | 2/2019 | Peatfield |
| 10,201,387 B2 | 2/2019 | Grace |
| 10,206,745 B2 | 2/2019 | Hendrick |
| 10,219,819 B2 | 3/2019 | Grace |
| 10,226,263 B2 | 3/2019 | Look |
| 10,236,952 B1 | 3/2019 | Sadot |
| 10,245,107 B2 | 4/2019 | Sierra |
| 10,258,792 B2 | 4/2019 | Archuleta |
| 10,265,520 B2 | 4/2019 | Grace |
| 10,271,904 B2 | 4/2019 | Islam |
| 10,285,726 B2 | 5/2019 | Nguyen |
| 10,305,244 B2 | 5/2019 | Sierra |

(56) References Cited

U.S. PATENT DOCUMENTS

| | | |
|---|---|---|
| 10,321,931 B2 | 6/2019 | Aljuri |
| 10,342,902 B2 | 7/2019 | Bagwell |
| 10,363,398 B2 | 7/2019 | Gerrans |
| 10,391,275 B2 | 8/2019 | Burnett |
| 10,405,924 B2 | 9/2019 | Bowe |
| 10,499,944 B2 | 12/2019 | Mallaby |
| 10,531,883 B1 | 1/2020 | Deville |
| 10,603,415 B2 | 3/2020 | Look |
| 10,702,292 B2 | 7/2020 | Look |
| 10,716,583 B2 | 7/2020 | Look |
| 10,716,880 B2 | 7/2020 | Culbert |
| 10,722,253 B2 | 7/2020 | Deville |
| 10,765,592 B2 | 9/2020 | Locke |
| 10,772,683 B2 | 9/2020 | Zabar |
| 10,792,103 B2 | 10/2020 | Zabar |
| 10,835,647 B2 | 11/2020 | Sherman |
| 10,835,711 B2 | 11/2020 | Yang |
| 10,993,731 B2 | 5/2021 | Leynov |
| 11,051,832 B2 | 7/2021 | Look |
| 11,090,117 B2 | 8/2021 | Zabar |
| 11,096,712 B2 | 8/2021 | Teigen |
| 11,197,683 B1 | 12/2021 | Teigen |
| 11,247,030 B2 | 2/2022 | Browd |
| 11,259,821 B2 | 3/2022 | Buck |
| 11,317,787 B2 | 5/2022 | Hillman |
| 11,337,712 B2 | 5/2022 | Teigen |
| 11,357,951 B2 | 6/2022 | Burnett |
| 11,369,435 B2 * | 6/2022 | Khan ............... A61B 34/30 |
| 11,400,255 B1 | 8/2022 | Chou |
| 11,406,402 B2 | 8/2022 | Deville |
| 11,432,835 B2 | 9/2022 | Shaffer |
| 11,464,528 B2 | 10/2022 | Brady |
| 11,471,582 B2 | 10/2022 | Yee |
| 11,490,909 B2 | 11/2022 | Look |
| 11,497,521 B2 | 11/2022 | Mallaby |
| 11,547,426 B2 | 1/2023 | Deville |
| 11,835,707 B2 | 12/2023 | Liang |
| 2001/0001314 A1 | 5/2001 | Davison |
| 2001/0016739 A1 | 8/2001 | Goldman |
| 2001/0016749 A1 | 8/2001 | Blatter |
| 2002/0016624 A1 | 2/2002 | Patterson |
| 2002/0045811 A1 | 4/2002 | Kittrell |
| 2002/0045890 A1 | 4/2002 | Celliers |
| 2002/0072680 A1 | 6/2002 | Schock |
| 2002/0095087 A1 | 7/2002 | Mourad |
| 2002/0173811 A1 | 11/2002 | Tu |
| 2002/0183729 A1 | 12/2002 | Farr |
| 2003/0009157 A1 | 1/2003 | Levine |
| 2003/0050686 A1 | 3/2003 | Raeder-Devens |
| 2003/0078568 A1 | 4/2003 | Caldera |
| 2003/0120256 A1 | 6/2003 | Lary |
| 2003/0125709 A1 | 7/2003 | Eidenschink |
| 2003/0125719 A1 * | 7/2003 | Furnish ............... A61B 1/07 606/15 |
| 2003/0171691 A1 | 9/2003 | Casscells |
| 2003/0181823 A1 | 9/2003 | Gatto |
| 2003/0181847 A1 | 9/2003 | Bruno-Raimondi |
| 2003/0181938 A1 | 9/2003 | Roth |
| 2003/0191460 A1 | 10/2003 | Hobbs |
| 2003/0199860 A1 | 10/2003 | Loeb |
| 2003/0199960 A1 | 10/2003 | Paskar |
| 2004/0044337 A1 | 3/2004 | Shafirstein |
| 2004/0093044 A1 | 5/2004 | Rychnovsky |
| 2004/0102766 A1 | 5/2004 | Poleo |
| 2004/0138562 A1 | 7/2004 | Makower |
| 2004/0142654 A1 | 7/2004 | Stammer |
| 2004/0162516 A1 | 8/2004 | Mandrusov |
| 2004/0193055 A1 | 9/2004 | Field |
| 2004/0236228 A1 | 11/2004 | Stoltz |
| 2005/0015123 A1 | 1/2005 | Paithankar |
| 2005/0020901 A1 | 1/2005 | Belson |
| 2005/0107738 A1 | 5/2005 | Slater |
| 2005/0113798 A1 | 5/2005 | Slater |
| 2005/0131400 A1 | 6/2005 | Hennings |
| 2005/0177132 A1 | 8/2005 | Lentz |
| 2005/0187537 A1 | 8/2005 | Loeb |
| 2005/0203497 A1 | 9/2005 | Speeg |
| 2005/0244101 A1 | 11/2005 | Kitabayashi |
| 2005/0251116 A1 | 11/2005 | Steinke |
| 2005/0288655 A1 | 12/2005 | Root |
| 2006/0069417 A1 | 3/2006 | Farley |
| 2006/0095015 A1 | 5/2006 | Hobbs |
| 2006/0095059 A1 | 5/2006 | Bleich |
| 2006/0106338 A1 | 5/2006 | Chang |
| 2006/0137345 A1 | 6/2006 | Cho |
| 2006/0142747 A1 | 6/2006 | Appling |
| 2006/0149218 A1 | 7/2006 | Slater |
| 2006/0189967 A1 | 8/2006 | Masotti |
| 2006/0229515 A1 | 10/2006 | Sharareh |
| 2006/0241495 A1 | 10/2006 | Kurtz |
| 2006/0241572 A1 | 10/2006 | Zhou |
| 2006/0253112 A1 | 11/2006 | Suarez |
| 2006/0264905 A1 | 11/2006 | Eskridge |
| 2007/0016068 A1 | 1/2007 | Grunwald |
| 2007/0016177 A1 | 1/2007 | Vaynberg |
| 2007/0073160 A1 | 3/2007 | Imam |
| 2007/0073268 A1 | 3/2007 | Goble |
| 2007/0073278 A1 | 3/2007 | Johnson |
| 2007/0123846 A1 | 5/2007 | Hennings |
| 2007/0129706 A1 | 6/2007 | Katoh |
| 2007/0135791 A1 | 6/2007 | Slater |
| 2007/0149985 A1 | 6/2007 | Cole |
| 2007/0167937 A1 | 7/2007 | Brown |
| 2007/0179485 A1 | 8/2007 | Yeik |
| 2007/0179486 A1 | 8/2007 | Welch |
| 2007/0179575 A1 | 8/2007 | Esch |
| 2007/0208400 A1 | 9/2007 | Nadkarni |
| 2007/0270688 A1 | 11/2007 | Gelbart |
| 2007/0299404 A1 | 12/2007 | Katoh |
| 2007/0299431 A1 | 12/2007 | Jakubowski |
| 2008/0015559 A1 | 1/2008 | Appling |
| 2008/0071333 A1 | 3/2008 | Hayes |
| 2008/0082091 A1 | 4/2008 | Rubtsov |
| 2008/0114428 A1 | 5/2008 | Trembly |
| 2008/0119869 A1 | 5/2008 | Teague |
| 2008/0146918 A1 | 6/2008 | Magnin |
| 2008/0154257 A1 | 6/2008 | Sharareh |
| 2008/0154293 A1 | 6/2008 | Taylor |
| 2008/0177183 A1 | 7/2008 | Courtney |
| 2008/0177186 A1 | 7/2008 | Slater |
| 2008/0188843 A1 | 8/2008 | Appling |
| 2008/0188910 A1 | 8/2008 | Spaide |
| 2008/0200873 A1 | 8/2008 | Espinosa |
| 2008/0208180 A1 | 8/2008 | Cartier |
| 2008/0221560 A1 | 9/2008 | Arai |
| 2008/0249399 A1 | 10/2008 | Appling |
| 2008/0262465 A1 | 10/2008 | Zinger |
| 2008/0275445 A1 | 11/2008 | Kelly |
| 2008/0300583 A1 | 12/2008 | Foley |
| 2008/0300662 A1 | 12/2008 | Taylor |
| 2008/0319418 A1 | 12/2008 | Chong |
| 2009/0018486 A1 | 1/2009 | Goren |
| 2009/0018603 A1 | 1/2009 | Mitelberg |
| 2009/0048607 A1 | 2/2009 | Rockley |
| 2009/0082760 A1 | 3/2009 | Zinn |
| 2009/0105654 A1 | 4/2009 | Kurth |
| 2009/0125007 A1 | 5/2009 | Splinter |
| 2009/0163899 A1 | 6/2009 | Burton |
| 2009/0182281 A1 | 7/2009 | Kurth |
| 2009/0209907 A1 | 8/2009 | Grata |
| 2009/0234344 A1 | 9/2009 | Lavender |
| 2009/0234378 A1 | 9/2009 | Escudero |
| 2009/0247823 A1 | 10/2009 | Yamamoto |
| 2009/0254078 A1 | 10/2009 | Just |
| 2009/0264875 A1 | 10/2009 | Appling |
| 2009/0299351 A1 | 12/2009 | Dadisman |
| 2010/0016857 A1 | 1/2010 | McKenna |
| 2010/0057056 A1 | 3/2010 | Gurtner |
| 2010/0069897 A1 | 3/2010 | Spikker |
| 2010/0125253 A1 | 5/2010 | Olson |
| 2010/0152720 A1 | 6/2010 | Sauro |
| 2010/0168572 A1 | 7/2010 | Sliwa |
| 2010/0168823 A1 | 7/2010 | Strisower |
| 2010/0191178 A1 | 7/2010 | Ross |

(56) References Cited

U.S. PATENT DOCUMENTS

| | | |
|---|---|---|
| 2010/0198150 A1 | 8/2010 | Michal |
| 2010/0198240 A1 | 8/2010 | Simpson |
| 2010/0198247 A1 | 8/2010 | Chang |
| 2010/0210995 A1 | 8/2010 | Jakubowski |
| 2010/0234925 A1 | 9/2010 | Harris |
| 2010/0280504 A1 | 11/2010 | Manzke et al. |
| 2010/0286791 A1 | 11/2010 | Goldsmith |
| 2010/0296531 A1 | 11/2010 | Hohm |
| 2010/0305475 A1 | 12/2010 | Hinchliffe |
| 2010/0305715 A1 | 12/2010 | Mathis |
| 2010/0312263 A1 | 12/2010 | Moberg |
| 2010/0318067 A1 | 12/2010 | Klima |
| 2011/0034922 A1 | 2/2011 | Thompson |
| 2011/0060300 A1 | 3/2011 | Weig |
| 2011/0134523 A1 | 6/2011 | Wu |
| 2011/0172586 A1 | 7/2011 | Hennings |
| 2011/0213446 A1 | 9/2011 | Tucek |
| 2011/0251519 A1 | 10/2011 | Romoscanu |
| 2011/0270238 A1 | 11/2011 | Rizq |
| 2012/0065490 A1 | 3/2012 | Zharov |
| 2012/0109191 A1 | 5/2012 | Marano, Jr. |
| 2012/0130415 A1 | 5/2012 | Tal |
| 2012/0265183 A1 | 10/2012 | Tulleken |
| 2012/0271170 A1 | 10/2012 | Emelianov |
| 2013/0005236 A1 | 1/2013 | Kim |
| 2013/0096545 A1 | 4/2013 | Laudenslager |
| 2013/0131643 A1 | 5/2013 | Parodi |
| 2013/0131644 A1 | 5/2013 | Parodi |
| 2013/0197306 A1 | 8/2013 | Armand |
| 2013/0211379 A1 | 8/2013 | Clair |
| 2013/0231660 A1 | 9/2013 | Edwards |
| 2013/0261614 A1 | 10/2013 | Appling |
| 2013/0274674 A1 | 10/2013 | Fischell |
| 2013/0304034 A1 | 11/2013 | Cabiri |
| 2013/0310680 A1 | 11/2013 | Werahera |
| 2013/0345541 A1 | 12/2013 | Nau, Jr. |
| 2014/0031800 A1 | 1/2014 | Ben Oren |
| 2014/0052114 A1 | 2/2014 | Ben-Oren |
| 2014/0081292 A1 | 3/2014 | Moll |
| 2014/0133814 A1 | 5/2014 | Stevens |
| 2014/0180034 A1 | 6/2014 | Hoseit |
| 2014/0188062 A1 | 7/2014 | James |
| 2014/0263207 A1 | 9/2014 | Liu |
| 2014/0276682 A1 | 9/2014 | Hendrick |
| 2014/0276689 A1* | 9/2014 | Grace ............... A61B 18/245 606/11 |
| 2014/0343482 A1 | 11/2014 | MacKay |
| 2014/0358134 A1 | 12/2014 | Appling |
| 2015/0038953 A1 | 2/2015 | Varghese |
| 2015/0057648 A1 | 2/2015 | Swift |
| 2015/0164573 A1 | 6/2015 | Delaney |
| 2015/0238091 A1 | 8/2015 | Iyer |
| 2015/0320480 A1* | 11/2015 | Cosman, Jr. ........ A61B 18/1482 606/34 |
| 2015/0359595 A1 | 12/2015 | Ben Oren et al. |
| 2016/0029902 A1 | 2/2016 | Smith |
| 2016/0135883 A1* | 5/2016 | Herscher ............ A61B 18/1206 606/41 |
| 2017/0100142 A1 | 4/2017 | Look |
| 2017/0246444 A1 | 8/2017 | Domatch |
| 2018/0028794 A1 | 2/2018 | Browd |
| 2018/0104390 A1 | 4/2018 | Kilcran |
| 2018/0207397 A1 | 7/2018 | Look |
| 2019/0015157 A1 | 1/2019 | Grace |
| 2019/0216476 A1 | 7/2019 | Barry |
| 2019/0290815 A1 | 9/2019 | Antonicelli |
| 2019/0336732 A1 | 11/2019 | Laudenslager |
| 2019/0343445 A1 | 11/2019 | Burnett |
| 2020/0009301 A1 | 1/2020 | Yee |
| 2020/0015840 A1 | 1/2020 | Mallaby |
| 2020/0022711 A1 | 1/2020 | Look |
| 2020/0179576 A1 | 6/2020 | Wood |
| 2020/0179578 A1 | 6/2020 | Look |
| 2020/0206457 A1 | 7/2020 | Boling |
| 2020/0281610 A1 | 9/2020 | Look |
| 2020/0289722 A1 | 9/2020 | Culbert |
| 2020/0297362 A1 | 9/2020 | Deville |
| 2020/0337772 A1 | 10/2020 | Ben-Oren |
| 2020/0367917 A1 | 11/2020 | Teigen |
| 2020/0397957 A1 | 12/2020 | Teigen |
| 2021/0038306 A1* | 2/2021 | McLoughlin ........ A61B 5/4869 |
| 2021/0069467 A1 | 3/2021 | Garrison |
| 2021/0093756 A1 | 4/2021 | Sherman |
| 2021/0109340 A1 | 4/2021 | Kaicheng |
| 2021/0128182 A1 | 5/2021 | Teigen |
| 2021/0315598 A1 | 10/2021 | Buck |
| 2022/0008090 A1 | 1/2022 | Look |
| 2022/0031930 A1 | 2/2022 | Downey |
| 2022/0096104 A1 | 3/2022 | Ogle |
| 2022/0152345 A1 | 5/2022 | Simiele |
| 2022/0152346 A1 | 5/2022 | Burnett |
| 2022/0176031 A1 | 6/2022 | Cheng |
| 2022/0193366 A1 | 6/2022 | Cheng |
| 2022/0211437 A1 | 7/2022 | Ben-Oren |
| 2022/0218365 A1 | 7/2022 | Deville |
| 2022/0257268 A1 | 8/2022 | Culbert |
| 2022/0280171 A1 | 9/2022 | Teigen |
| 2022/0338887 A1 | 10/2022 | Nair |
| 2022/0339338 A1 | 10/2022 | Nair |
| 2022/0339339 A1 | 10/2022 | Nair |
| 2022/0378443 A1 | 12/2022 | Look |
| 2022/0378450 A1 | 12/2022 | Culbert |
| 2022/0379081 A1 | 12/2022 | Look |
| 2022/0379082 A1 | 12/2022 | Look |
| 2022/0379083 A1 | 12/2022 | Look |
| 2022/0379084 A1 | 12/2022 | Look |
| 2022/0379085 A1 | 12/2022 | Look |
| 2022/0379086 A1 | 12/2022 | Look |
| 2022/0387052 A1 | 12/2022 | Look |
| 2022/0387752 A1 | 12/2022 | Look |
| 2022/0387753 A1 | 12/2022 | Look |
| 2023/0026412 A1 | 1/2023 | Teigen |
| 2023/0099283 A1 | 3/2023 | Deville |
| 2023/0100426 A1 | 3/2023 | Deville |
| 2023/0301708 A1 | 9/2023 | Mickelsen |
| 2023/0329780 A1 | 10/2023 | Liu |
| 2023/0408329 A1 | 12/2023 | Zabar |

FOREIGN PATENT DOCUMENTS

| | | |
|---|---|---|
| CA | 3105728 A1 | 1/2020 |
| CN | 1049287 A | 2/1991 |
| CN | 1261774 A | 8/2000 |
| CN | 2713994 | 8/2005 |
| CN | 101170959 | 4/2008 |
| CN | 101795630 | 8/2010 |
| CN | 112533550 A | 3/2021 |
| DE | 8905642 U1 | 8/1989 |
| DE | 60316175 T2 | 5/2008 |
| EP | 0311295 A2 | 4/1989 |
| EP | 0341943 | 11/1989 |
| EP | 1567082 | 8/2005 |
| EP | 1610855 A2 | 1/2006 |
| EP | 1709987 | 10/2006 |
| EP | 2226031 A1 | 9/2010 |
| EP | 2399507 | 12/2011 |
| EP | 3025175 A1 | 6/2016 |
| EP | 3423124 A4 | 10/2019 |
| EP | 3806757 A4 | 5/2022 |
| GB | 1533204 A | 11/1978 |
| IL | 224434 A | 12/2016 |
| JP | H01178011 | 7/1989 |
| JP | 2021532850 A | 12/2021 |
| KR | 20210035811 A | 4/2021 |
| WO | 9214515 A1 | 9/1992 |
| WO | 9509575 A1 | 4/1995 |
| WO | 9834673 | 8/1998 |
| WO | 0245601 A1 | 6/2002 |
| WO | 03057060 A1 | 7/2003 |
| WO | 2004021886 A1 | 3/2004 |
| WO | 2004043280 A1 | 5/2004 |
| WO | 2007125638 | 11/2007 |
| WO | 2008124790 | 10/2008 |
| WO | 02011107117 A1 | 9/2011 |

(56) References Cited

FOREIGN PATENT DOCUMENTS

| WO | 2012114333 A1 | 8/2012 |
|---|---|---|
| WO | 2012114334 A1 | 8/2012 |
| WO | 2012151396 | 11/2012 |
| WO | 2013172970 A1 | 11/2013 |
| WO | 2014118738 A1 | 8/2014 |
| WO | 2017155994 A1 | 9/2017 |
| WO | 2018019829 A1 | 2/2018 |

OTHER PUBLICATIONS

Kabnick, et al, EVL Ablation Using Jacket-Tip Laser Fibers, Endovascular Today, Jul. 2009, pp. 77-81.
Leopardi, et al, Systematic Review of Treatments for Varicose Veins, Ann Vasc Surg 2009: 23:264-276.
Litvack, et al, (1988) Pulsed laser angioplasty: wavelength power and energy dependencies relevant to clinical application. Lasers Surg Med 8(1): 60-65.
Mackay, et al, Saphenous Vein Ablation, Endovascular Today, Mar. 2006, pp. 44-48.
Memetoglu, et al, Combination Technique of Tumescent Anesthesia During Endovenous Laser Therapy of Saphenous Vein Insufficiency, Interactive Cardiovascular and Thoracic Surgery 11, 2010, pp. 774-778.
Min, et al, Endovenous Laser Treatment of Saphenous Vein Reflux: Long-Term Results, J Vasc Interv Radiol 2003, 14:991-996.
Min, et al, Endovenous Laser Treatment of the Incompetent Greater Saphenous Vein, J Vasc Interv Radiol 2001, 12:1167-1171.
Murphy-Chutorian et al., (1985) Selective absorption of ultraviolet laser energy by human atherosclerotic plaque treated with tetracycline. Am J Cardiol 55(11): 1293-1297.
Neev, Joseph, Ph. D., Two-Lasers Assisted Ablation: A Method for Enhancing Conventional Laser Ablation of Materials, Lasers in Surgery and Medicine 19:130-134 (1996).
Notice of Allowance dated Oct. 5, 2022 for U.S. Appl. No. 16/436,650 (pp. 1-8).
Notice of Allowance dated Dec. 21, 2022 for U.S. Appl. No. 16/094,137 (pp. 1-7).
Notice of Allowance dated Apr. 13, 2021 for U.S. Appl. No. 17/123,205 (pp. 1-8).
Notice of Allowance dated Aug. 10, 2020 for U.S. Appl. No. 16/655,864 (pp. 1-9).
Notice of Allowance dated Aug. 6, 2020 for U.S. Appl. No. 16/592,725 (pp. 1-9).
Notice of Allowance dated Jul. 26, 2021 for U.S. Appl. No. 16/189,297 (pp. 1-8).
Notice of Allowance dated Jun. 10, 2022 for U.S. Appl. No. 16/436,650 (pp. 1-7).
Notice of Allowance dated May 10, 2021 for U.S. Appl. No. 17/076,032 (pp. 1-8).
Office Action dated Oct. 4, 2022 for U.S. Appl. No. 14/764,180 (pp. 1-21).
Office Action dated Dec. 28, 2022 for U.S. Appl. No. 16/839,523 (pp. 1-11).
Office Action dated Apr. 15, 2021 for U.S. Appl. No. 16/189,297 (pp. 1-8).
Office Action dated Apr. 29, 2020 for U.S. Appl. No. 16/094,137 (pp. 1-12).
Office Action dated Aug. 3, 2021 for U.S. Appl. No. 16/436,650 (pp. 1-11).
Office Action dated Dec. 11, 2020 for U.S. Appl. No. 16/189,297 (pp. 1-7).
Office Action dated Feb. 15, 2022 for U.S. Appl. No. 16/436,650 (pp. 1-13).
Office Action dated Feb. 24, 2021 for U.S. Appl. No. 17/123,205 (pp. 1-4).
Office Action dated Jan. 31, 2022 for U.S. Appl. No. 16/436,650 (pp. 1-11).
Office Action dated Jul. 13, 2022 for U.S. Appl. No. 16/839,523 (pp. 1-9).
Office Action dated Jun. 9, 2020 for U.S. Appl. No. 16/189,297 (pp. 1-10).
Office Action dated Jun. 26, 2020 for U.S. Appl. No. 14/764,180 (pp. 1-16).
Office Action dated Mar. 2, 2021 for U.S. Appl. No. 16/436,650 (pp. 1-16).
Office Action dated Mar. 23, 2021 for U.S. Appl. No. 17/123,205 (pp. 1-3).
Office Action dated May 6, 2022 for U.S. Appl. No. 14/764,180 (pp. 1-16).
Office Action dated May 28, 2021 for U.S. Appl. No. 16/366,434 (pp. 1-12).
Office Action dated Sep. 2, 2020 for U.S. Appl. No. 16/436,650 (pp. 1-19).
Office Action dated Sep. 30, 2021 for U.S. Appl. No. 14/764,180 (pp. 1-16).
Office Action dated Sep. 9, 2020 for U.S. Appl. No. 16/094,137 (pp. 1-11).
Oraevsky, Alexander A., Plasma Mediated Ablation of Biological Tissues with Nanosecond-to-Femtosecond Laser Pulses: Relative Role of Linear and Nonlinear Absorption, IEEE Journal of Selected Topics in Quantum Electronics, vol. 2, No. 4, Dec. 1996, 9 pages.
Pace, E., et al, Fast Stable Visible-blind and Highly Sensitive CVD Diamond UV Photo Detectors for Laboratory and Space Applications, Diamond and Related Materials, vol. 9, Issues 3-6 (Apr.-May 2000) pp. 987-993.
Pandya et al (2015) Radiofrenquency ablation of pancreatic ductal adenocarcinoma: The past, the present and the future, World Journal of Gastrointestinal Oncology, Feb. 15, 2015, vol. 7, No. 2, pp. 6-11.
Papaioannou, Thanassis, et al., Excimer Laser Assisted Thrombolysis: The Effect of Fluence, Repetition Rate, and Catheter Size, Lasers in Surgery: Advanced Characterization, Therapeutics, and systems XII, Kenneth E. Bartels et al., Editors, Proceedings of SPIE vol. 4609 (2002), 6 pages.
Papaioannou, Thanassis, et al., Particulate debris analysis during excimer laser thrombolysis: An in-vitro study., Lasers in Surgery: Advanced Characterization, Therapeutics, and systems XII, Kenneth E. Bartels et al., Editors, Proceedings of SPIE vol. 4609 (2002), 9 pages.
Park, et al, Fluoroscopy-Guided Endovenous Foam Sclerotherapy Using a Microcatheter in Varicose Tributaries Followed by Endovenous Laser Treatment of Incompetent Saphenous Veins: Technocal Feasibility and Early Results, Dermatol Surg 2009, 35:804-812.
Partial European Search Report, EP19177412, Jul. 17, 2019, 1 page.
Pories and Albrecht (2001) Etiology of type II diabetes mellitus: role of the foregut. World J Surg 25(4): 527-31.
Pories et al., (2011) The surgical treatment of type two diabetes mellitus. Surg Clin North Am 91(4): 821-36.
Prince, M.R., et al, Preferential Light Absorption in Atheromas in Vitro—Implications for Laser Angioplasty, J of Clin Investigation, vol. 78(1) (Jul. 1986) pp. 295-302.
Proebstle, et al, Thermal Damage of the Inner Vein Wall During Endovenous Laser Treatment: Key Role of Energy Absorption by Intravascular Blood, Dermatol Surf 2002:28596-600.
Proebstle, et al, Treatment of the Incompetent Great Saphenous Vein by Endovenous RF Powered Segmental Therman Ablation: First Clinical Experience, Journal of Vascular Surgery, 2008, pp. 151-156.e1.
Richou, B, et al., Delivery of 10-mw Nd:YAG Laser Pulses by Large Core Optical Fibers: Dependence of the Laser-Itensity Profile on Beam Propagation, Applied Optics, vol. 36, No. 7 (1997) pp. 1610-1614.
Albagli, D., et al., Time Dependence of Laser-Induced Surface Breakdown in Fused Silica at 355nm in the Nanosecond Regime, SPIE vol. 1441, Laser Induced Damage in Optical Materials, 1990, 8 pages.
Alexander (1991) Tissue pathologies uncovered by spectral analysis. J Clin Laser Med Surg 9(4): 238-241.
Almeida, et al, RF Endovenous ClosureFAST Versus Laser Ablation for the Treatment of Great Saphenous Reflux: A Multicenter, Single-blinded, Randomized Study, J Vasc Interv Radiol 2009, 20:752-759.

(56) References Cited

OTHER PUBLICATIONS

Ambrosini, V. et al., Excimer laser in acute myocardial infarction: Single centre experience on 66 patients, International Journal of Cardiology 127 (2008) 98-102.
Chinese Office Action for App. No. CN2017103395497, dated Apr. 3, 2021, 7 pages.
Chong, et al, Technical Tip: Cold Saline Infiltration Instead of Local Anaesthetic in Endovenous Laser Treatment, Phlebology vol. 21 No. 2, 2006, oo 88-89.
Coe, M. Sean, et al., Excimer Laser Lead Extraction Catheter with Increased Laser Parameters, Lasers in Surgery: Advanced Characterization, Therapeutics, and Systems XI, R. Rox Anderson et al., Editors, Proceedings of SPIE vol. 4244 (2001), 8 pages.
Cordis® Outback® Re-Entry Catheter, Chronic Total Occlusion (CTO) Technologies brochure, Dec. 2008.
Corrected Notice of Allowance dated Nov. 5, 2021 for U.S. Appl. No. 16/189,297 (pp. 1-5).
Cummings et al., (2004) Gastric bypass for obesity: mechanisms of weight loss and diabetes resolution. J Clin Endocrinol Metab 89(6): 2608-15.
DiMatteo, et al (2010) EUS-guided Nd: YAG laser ablation of normal pancreatic tissue: a pilot study in a pig model, Gastrointest. Endosc. 72(2): 358-63.
Doganci, et al, Comparison of 980 nm Laser and Bare-tip Fibre with 1470 nm Laser and Radial Fibre in the Treatment of Great Saphenous Vein Varicosities: A Prospective Randomised Clinical Trial, Eur J Vasc Endovasc Surg, 2010, pp. 254-259.
Du, etal, PhotochemCAD: A Computer-Aided Design and Reseach Tool in Photochemistry, Photochemisty and Photobiology, 1998, 68(2), pp. 141-142.
Dunst, et al, Diffuse Phlegmonous Phlebitis After Endovenous Laser Treatment of the Greater Saphenous Vein, Journal of Vascular Surgery, vol. 43 No. 5, 2006, pp. 1056-1058.
Elias, et al, Treating the Small Saphenous Vein, Endovascular Today, Aug. 2008, pp. 60-64.
Endovascular Today, Supplement to Endovascular Today, Nov./Dec. 2004, pp. S1-S35.
English Language Version of the Technical Report Issued for Brazilian Patent App. No. BR1120130214635, dated Jan. 4, 2021, 5 pages.
Esenaliev, R.O., et al, Laser Ablation of Atherosclerotic Blood Vessel Tissue Under Various Irradiation Conditions, IEEE Transactions on Biomedical Engineering, vol. 36, No. 12, (Dec. 1989) pp. 1188-1194.
European Patent Office Communication pursuant to Article 94(3) EPC for App. No. EP12750139.3, dated Jun. 11, 2021, 5 pages.
European Search Opinion, PCT/IB2014058688, Dec. 2, 2016, 10 pages.
European Search Report, EP19177412, Oct. 28, 2019, 3 pages.
European Search Report, PCT/IL2015050480, Apr. 13, 2017, 7 pages.
Fleischer and Sharma (2008) Endoscopic Ablation of Barrett's Esophagus Using the Halo System. Dig Dis 26(4): 280-284.
Fleischer and Sharma (2009) Endoscopic Ablation of Barrett's Esophagus Using the Halo® System. Dig Dis 26(4): 280-284.
Fleischer and Sharma, Endoscopic Ablation of Barrett's Esophagus Using the Halo® System. Mönkemüller K, Wilcox CM, Muñoz-Navas M (eds):Interventional and Therapeutic Gastrointestinal Endoscopy. Front Gastrointest Res. Basel, Karger, 2010, vol. 27, pp. 140-146.
Grundfest et al., (1985) Pulsed ultraviolet lasers and the potential for safe laser angioplasty. Am J Surg 150(2): 220-226.
Herzog, Amir et al., Spatial-coherence effect on damage occurrence in multimode optical fibers using nanosecond pulses, Advanced Photonics © 2014 OSA, 1 page.
Hongbao, Ma et al., Interaction of excimer laser with blood components and thrombosis, Life Science Journal, vol. 5, Mo 3, 2008, 8 pages.
International Preliminary Report on Patentability, PCT/IB2014/ 058688, Apr. 8, 2015, 7 pages.
International Preliminary Report on Patentability, PCT/IL2012/ 000088, Aug. 27, 2013, 10 pages.
International Preliminary Report on Patentability, PCT/IL2012/ 000089, Aug. 27, 2013, 9 pages.
International Preliminary Report on Patentability, PCT/IL2015/ 050480, Nov. 8, 2016, 8 pages.
International Preliminary Report on Patentability, PCT/IL2015/ 050529, Nov. 22, 2016, 6 pages.
International Preliminary Report on Patentability, PCT/IL2017/ 050498, Nov. 6, 2018, 7 pages.
International Search Report 03763292_SESR, dated Jan. 28, 2010.
International Search Report 04256733 ESR, dated Jan. 14, 2005.
International Search Report EP03252158_AESR dated Aug. 29, 2003, 1 page.
International Search Report for PCT/IL2015/050480 Completed Oct. 19, 2015; Mailed Oct. 21, 2015, 6 pages.
International Search Report PCT-US-03-21213 ISR, dated Mar. 29, 2004.
International Search Report PCT-US-08-059791 IPRP, dated Nov. 4, 2008.
International Search Report PCT-US-08-059791 ISR, dated Nov. 4, 2008.
International Search Report PCT-US-08-059791 WOSA, Nov. 4, 2008.
International Search Report PCT/IL2017/050498 Completed Aug. 15, 2017; Mailed Sep. 10, 2017, 4 pages.
International Search Report, PCT/IB2014/058688, Jun. 15, 2014, 5 pages.
International Search Report, PCT/IL2012/000088, Jul. 17, 2012, 2 pages.
International Search Report, PCT/IL2012/000089, Jul. 13, 2012, 2 pages.
International Search Report, PCT/IL2015/050529, Sep. 16, 2015, 5 pages.
International Search Report, PCT/IL2017/050498, Nov. 17, 2017, 4 pages.
Jackson (2009) High-power and highly efficient diode-cladding-pumped holmium-doped flouride fiber laster operating at 2.94 microm. Opt Lett 34(15):2327-2329.
Jackson et al., (2007) Directly diode-pumped holmium fiber lasers. Optics Letters 32(17): 2496-2498.
Ronkainen et al., (2005) Prevalence of Barrett's esophagus in the general population: an endoscopic study. Gastroenterology 129(6): 1825-1831.
Ronkainen, Jukka, et al., Prevalence of Barrett's Esophagus in the General Population: An Endoscopic Study, Gastroenterology 2005; 129:1825-1831.
Rubino and Gagner (2002) Potential of surgery for curing type 2 diabetes mellitus. Ann Surg 236(5): 554-559.
Rubino and Marescaux (2004) Effect of duodenal-jejunal exclusion in a non-obese animal model of type 2 diabetes: a new perspective for an old disease. Ann Surg 239(1): 1-11.
Rubino et al, (2006) The mechanism of diabetes control after gastrointestinal bypass surgery reveals a role of the proximal small intestine in the pathophysiology of type 2 diabetes. Ann Surg 244(5): 741-749.
Rubino et al., (2004) The early effect of the Roux-en-Y gastric bypass on hormones involved in body weight regulation and glucose metabolism. Ann Surg 240(2): 236-42.
Schmedt, et al, Evaluation of Endovenous RF Ablation and Laser Therapy with Endoluminal Optical Coherence Tomography in an Ex Vivo Model, Journal of Vasc Surg, 2007, pp. 1047-1058.
Schmidt-Uhling, T, et al, New Simplified Coupling Scheme for the Delivery of 20MW Nd:YAG Laser Pulses by Large Core Optical Fibers, Applied Physics B, Lasers and Optics, vol. 72, (2001) pp. 183-186.
Schwarz, et al, Endovenous Laser Ablation of Varicose Veins with the 1470-nm Diode Laser, Journal of Vasc Surg vol. 51, No. 6, pp. 1474-1478. (2010).
Schwarzwälder and Zeller (2010) Debulking procedures: potential device specific indications. Tech Vasc Interv Radiol 13(1): 43-53.

(56) References Cited

OTHER PUBLICATIONS

Shangguan, HanQun, et al., Microsecond Laser Ablation of Thrombus and Gelatin Under Clear Liquids: Contact Versus Noncontact, IEEE Journal of Selected Topics in Quantum Electronics, vol. 2, No. 4, Dec. 1996, 8 pages.
Shuto, et al, Fiber Fuse Phenonmenon in Step-Index Single-Mode Optical Fibers, IEEE Journal of Quantum Electronics, vol. 40, No. 8, 2004, pp. 1113-1121.
Sikorska and Pan (2004) The Effect of Waveguide Material and Shape on Acoustic Emission Transmission Characteristics, Part 1: Traditional Features. Journal of Acoustic Emission 22: 264-273.
Skorczakowski et al., (2010) Mid-infrared Q-switched Er:YAG laser for medical applications. Laser Physics Letters 7(7): 498-504.
Smucler, et al, Invasive Leg Veins Treatment with 1064/1319 Nd:YAG Laser/Combination with Dye Laser Treatment, SPIE vol. 3590, pp. 78-87. (1999).
Supplementary European Search Report, EP15789895, Apr. 13, 2017, 2 pages.
Supplementary European Search Report, EP15796468, May 10, 2017, 2 pages.
Supplementary European Search Report, PCT/IB2014058688, Aug. 26, 2016, 7 pages.
Supplementary European Search Report, PCT/IL2012000088, Sep. 30, 2014, 8 pages.
Tabbara, et al, Laser-Fused Biologic Vascular Graft Anastomoses, Journal of Investigative Surgery, 6:3, 289-295. (1993).
Taylor, et al, Long Saphenous Vein Stripping Under Local Anaesthesia, Annals of the Royal College of Surgeons of England, 1981, vol. 63, pp. 206-207.
Taylor, Rod S., et al, Dependence of the XeCl Laser Cut Rate of Plaque on the Degree of Calcification, Laser Fluence, and Optical Pulse Duration, Lasers in Surgery and Medicine, vol. 10, Issue 5, (1990) pp. 414-419.
Topaz, On, M.D. et al., "Optimally Spaced" Excimer Laser Coronary Catheters: Performance Analysis, Journal of Clinical Laser Medicine & Surgery vol. 19, No. 1, 2001, Mary Ann Liebert, Inc., pp. 9-14.
Verdam et al., (2012) An update on less invasive and endoscopic techniques mimicking the effect of bariatric surgery. J Obes 2012:597871, pp. 1-11.
Vuylsteke, et al, Intraluminal Fibre-Tip Centring Can Improve Endovenous Laser Ablation: A Histological Study, Eur J Vase Endovasc Surg, 2009, pp. 1-7.
Wang et al., (2013) Total transmission and total reflection of acoustic wave by zero index metamatehals loaded with general solid defects. Journal of Applied Physics 114(19): 194502, pp. 1-5.
Written Opinion of the International Searching Authority PCT/IL2017/050498; Mailed Sep. 10, 2017, 6 pages.
Written Opinion of the International Searching Authority, PCT/IL2012/000089, Jul. 13, 2012, 8 pages.
Written Opinion of the International Searching Authority, PCT/IL2014/058688, Jun. 15, 2014, 6 pages.
Written Opinion of the International Searching Authority, PCT/IL2015/050480, Oct. 21, 2015, 7 pages.
Written Opinion of the International Searching Authority, PCT/IL2015/050529, Sep. 16, 2015, 5 pages.
Written Opinion of the International Searching Authority, PCT/IL2017/050498, Nov. 9, 2017, 6 pages.
European Notice of Allowance issued in App. No. EP19177412, dated Nov. 22, 2023, 40 pages.
International Preliminary Report on Patentability issued in App. No. PCT/IB2022/061041, dated May 30, 2024, 17 pages.

\* cited by examiner

DYNAMIC LASER STABILIZATION AND CALIBRATION SYSTEM

CROSS-REFERENCE TO RELATED APPLICATIONS

This application is a continuation of, claims the benefit of and priority to, previously filed U.S. Provisional Patent Application Ser. No. 63/075,480 entitled "DYNAMIC CONTROL DEVICE AND METHOD OF USE FOR LASER DEVICE" filed on Sep. 8, 2020, the subject matter of which is hereby incorporated by reference in its entirety.

BACKGROUND

Lasers suffer from the need to be stabilized. Said differently, the laser medium (e.g., crystals, glass, semiconductors, or the like) of the laser needs time to stabilize once lasing starts. For example, many modern commercial lasers require around 30 minutes after turn-on for the laser medium to stabilize such that the energy emitted by the laser will not fluctuate over time, or will fluctuate within an acceptable tolerance.

Furthermore, lasers are often sensitive to changes in temperature. That is, as the temperature of the environment in which the laser is operating changes (e.g., room temperature, or the like) this impacts the efficiency of the laser. As a specific, non-limiting example, when room temperature surrounding the laser drops, the efficiency of the laser and the energy emitted by the laser may increase. However, the relationship between operating environment temperature and its impact on efficiency and/or laser energy varies between different types of lasers and laser mediums such that the impact of temperature of laser output cannot be compensated for, even when the variability in temperature is known.

Another issue with lasers is that as components within the laser (e.g., the laser medium, the lamps or pump lights, or the like) age, the energy emitted by the laser changes. These changes are difficult to account for as components often age at different rates and the degradation of the components and its effects on the emitted laser beam can depend on many factors besides just "on-time." For example, for high power lasers the initial pulses will typically have higher energy as the temperature in the laser is colder in the beginning than during a steady state operation.

As such, there is a need to stabilize the energy emitted by a laser or said differently to reduce the fluctuations in emitted energy due to, for example, start-up of the laser, changes in operating environment temperature, aging or degradation of laser components, or the like. More specifically, there is a need to dynamically control fluctuation of the laser output to reduce the potential for undesirable power distribution of the energy emitted by the laser during initial turn-on; during use of the laser; during stabilization of the laser; and/or even after stabilization of the laser to avoid changes in the laser output.

There is also a need to avoid exposure of pulses with high energy at any stage of operation of the laser, and especially in the first laser pulses when after a physician activates the laser in proximity to a tissue lesion. More specifically, avoiding exposure of pulses with high energy at any stage of operation of the laser will increase the likelihood of survivability of a fiber bundle used to deliver the laser energy during a treatment procedure.

BRIEF SUMMARY

The present disclosure describes a laser and a sensor to measure energy of emissions from the laser. Further, the present disclosure provides systems and methods to dynamically control, in real-time based on output from the sensor, the energy level of the laser to increase the stability of the laser, provide for usage of the laser before conventional stabilization times have elapsed, account for effects on laser energy output due to changes in operating environment temperature as well as degradation or age of components of the laser.

In many applications, lasers are within specification or tolerance if the emitter laser energy is within 20% of the specified laser energy. However, many modern applications of lasers, such as, medical procedures for ablation, require finer grained control of the emitted laser energy. This is particularly true where the effects of the procedure are non-linear. That is, a reduction of 20% in laser energy may reduce the ablation efficiency by more than 20%. More particularly for some ablation procedures, emitted laser energy less than a specific level will not result in efficient ablation. For example, a cold ablation (i.e., the mechanism of action for cellular death is non-thermal) requires certain energy level thresholds and if the emitted laser energy is outside of the required threshold it may result in undesirable treatment results, such as thermal ablation, an incomplete ablation, or other undesirable effects.

Accordingly, the systems and methods of the present disclosure are provided to calibrate a laser and further to monitor and control laser energy output during an ablation procedure to maintain a required ablation or energy output threshold. It is to be appreciated that the calibration and dynamic control techniques of the present disclosure provide for stabilization of the laser faster and with less fluctuations than with conventional techniques. A benefit to the systems and methods of the present disclosure is that the laser can be stabilized even in the presence of changes in operating environment temperature or to account for degradation of emitted laser energy due age of components of the laser system.

Additionally, the present disclosure is provided to monitor and control laser energy output to allow the laser to be used shortly after it is turned on with less fluctuations in emitted energy than conventionally possible. Furthermore, the present disclosure provides to monitor and control laser energy output for increased stability during operation than is conventionally possible. It is to be appreciated that this provides a significant advantage, particularly for medical ablation procedures as fluctuations in the energy emitted by the laser (e.g., resulting from laser stabilization or changes in operating room temperature, or the like) are reduced, thereby reducing possible unwanted damage to the tissue being ablated. Another benefit to the systems and methods of the present disclosure is that damage to the fiber in the catheter (e.g., from energy emission spikes during laser medium stabilization, or the like) is reduced due to the stabilization techniques described herein.

These and other examples are described in greater detail below. In the following description, numerous specific details such as processor and system configurations are set forth in order to provide a more thorough understanding of the described embodiments. However, the described embodiments may be practiced without such specific details. Additionally, some well-known structures (e.g., circuits, specific treatment protocols, and the like) have not been shown in detail, to avoid unnecessarily obscuring the described embodiments.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

As noted above, the present disclosure provides systems and methods to both calibrate a laser for use in an ablation procedure as well as to dynamically control a laser during an ablation procedure. Prior to describing illustrative embodiments of the configuration and dynamic control procedures, an example laser system that can be used with embodiments of the present disclosure is provided.

Figure 1A:
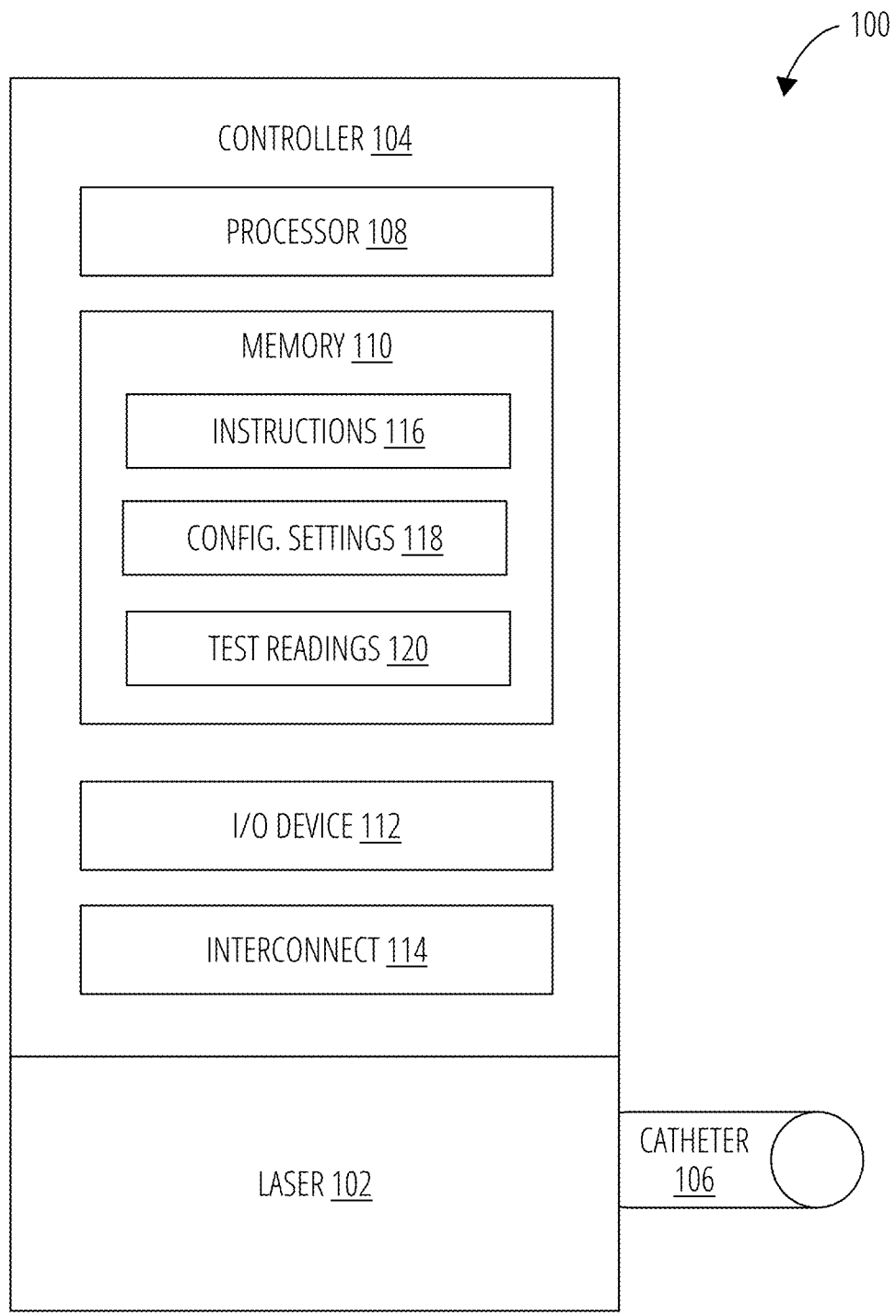
FIG. 1A illustrates a laser ablation system in accordance with embodiment(s).

FIG. 1A illustrates a laser ablation system 100 in accordance with non-limiting example(s) of the present disclosure. In general, laser ablation system 100 is arranged to deliver high power pulsed laser energy through optical fibers to ablate tissue or other material. For example, laser ablation system 100 can be used to deliver laser energy to ablate lesions on or in a body of a patient (not shown). Laser ablation system 100 includes a laser 102, a controller 104, and a catheter 106. Controller 104 includes a processor 108, a memory 110, an I/O device 112, and an interconnect 114. The memory 110 includes instructions 116, configuration settings 118, and test readings 120. One example of a laser ablation system, such laser ablation system 100 along with examples of the energy to be delivered by such a system, is described in U.S. patent application Ser. No. 15/309,193, which is incorporated herein by reference.

In general, a physician can use the laser ablation system 100 to deliver, via catheter 106, laser energy generated by laser 102 to a lesion or tissue of a patient to ablate the lesion or tissue as part of an ablation procedure. It is noted that the present disclosure can be applied to a variety of laser ablation procedures and types of lasers. In general however, the present disclosure is particularly applicable to pulsed lasers. By way of non-limiting example, laser 102 could be a solid state Nd:YAG laser arranged to output a pulsed laser beam and couple to catheter 106 to deliver laser radiation (or light) to tissue as part of an ablation procedure.

Figure 1B:
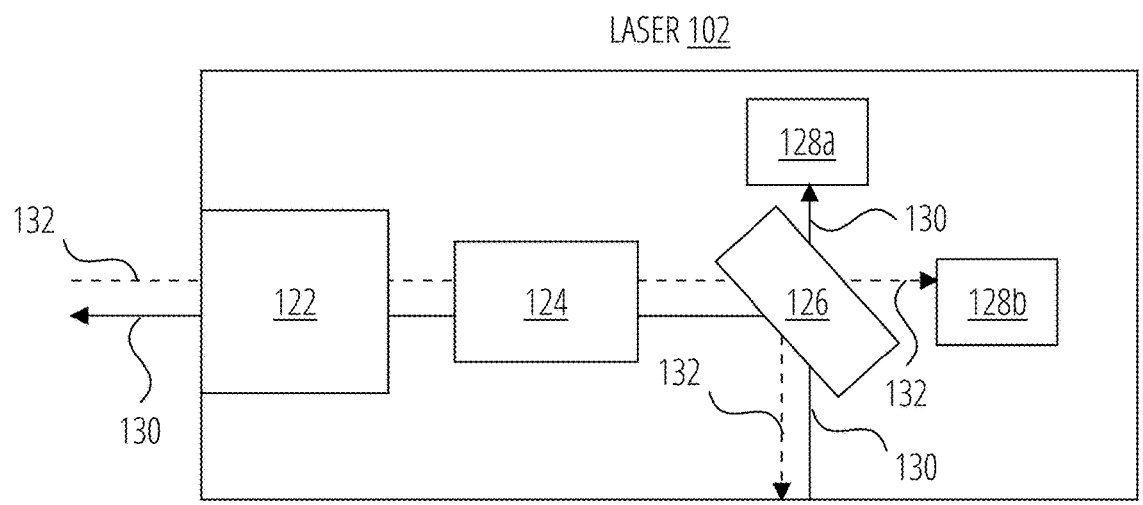
FIG. 1B illustrates a portion of the laser ablation system of FIG. 1A in greater detail in accordance with embodiment(s).

FIG. 1B illustrates a portion of laser 102 in accordance with non-limiting example(s) of the present disclosure. As depicted, laser 102 includes catheter connector housing 122, coupling optics 124, mirror 126, and a first sensor 128a and a second sensor 128b. Catheter connector housing 122 mechanically and optically couples with a catheter (e.g., catheter 106, or the like). During operation, laser 102 can generate laser beam 130, which is directed towards coupling optics 124 via mirror 126. Coupling optics 124 focuses laser beam 130 such that laser beam 130 is optically coupled to catheter connector housing 122 and catheter 106. It is to be appreciated that a portion of laser beam 130 will not be reflected by mirror 126 but will instead pass through mirror 126 and be incident on the first sensor 128a. First sensor 128a is arranged to measure an amount of energy or a magnitude of laser beam 130.

With some examples, mirror 126 can be more reflective to one type of polarization (e.g., P polarization or S polarization) while being less reflective to the other type of polarization. For example, mirror 126 can be configured to be approximately 99.5% reflective to light having an S polarization and approximately 99.2% reflective to light having a P polarization. As such, although the majority of laser beam 130 will be reflected by mirror 126, a small portion (e.g., <1%) of laser beam 130 will be transmitted through mirror 126 and be incident on the first sensor 128a. However, where mirror 126 is more reflective to a particular polarization as stated in the example above, the energy measured by the first sensor 128a will be based more on the particular polarization component with which the mirror 126 is less reflective. For example, in the above example the mirror 126 is more reflective to an S polarization component and as such the energy measured by the first sensor 128a is based on an P polarization component. In general, laser 102 can include a laser source (not shown) and a system of optical components and mirrors (also not shown) arranged to generate laser beam 130. The system of optical components and mirrors can, in some embodiments, split the laser beam 130 into polarization components, while and one polarization component can have a longer path to mirror 126 than the other polarization component. In such embodiments, the mirror 126 can be configured to be less reflective to the polarization component with the shortest path from laser source to the mirror 126. As a result, the energy measured by the first sensor 128a can be based less upon the system of optical components and mirrors and more upon the energy in the laser beam generated by the laser source.

Furthermore, during operation, some portion of laser beam 130 may be reflected (e.g., by the catheter 106) and transmitted back into laser 102. Second sensor 128b is arranged to measure an amount of energy or a magnitude of a reflection beam 132 (as described in more detail below).

Figure 1C:
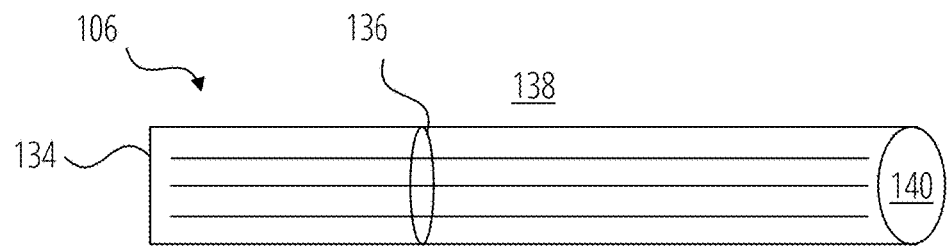
FIG. 1C illustrates a catheter for use with the laser ablation system of FIG. 1A in greater detail in accordance with embodiment(s).

FIG. 1C illustrates a more detailed embodiment of catheter 106. A more detailed example of a catheter for use with a laser ablation system, such as catheter 106, is described in U.S. patent application Ser. No. 16/436,650, which is incorporated herein by reference. As can be seen, catheter 106 includes a coupling end 134 at a proximal end of the catheter 106, the coupling end 134 is arranged to mechanically and optically couple with catheter connector housing 122. In some embodiments, catheter connector housing 122 is arranged to output laser beam 130 having a particular geometric shape, such as, square, rectangular, circular, oval, or the like. Likewise, coupling end 134 of catheter 106 can be arranged to receive the laser beam 130 having the same particular geometric shape as the connector housing 122.

With some examples, coupling end 134 can include identification circuitry (e.g., a radio frequency identification (RFID) transmitter, or the like). In some embodiments, connector housing 122 can include circuitry (not shown) to receive signals from a transmitted (e.g., an RFID transmitted embedded in catheter 106, or the like) disposed in or adjacent to coupling end 134. With some examples, the circuitry in connector housing can be arranged to receive an indication of a unique identifier (e.g., serial number, or the like) from the catheter 106 and determine whether the catheter 106 is authorized for use (e.g., from a valid source, the serial number has not already been used in a procedure, is not expired or past a certain expiration date, or the like). In some embodiments, memory 110 can include indications of authorized serial numbers and serial numbers that have been used, which processor 108 in executing instructions 116 can updated (e.g., based on completed procedures, from another database, from a network, or the like).

Catheter 106 further includes optical fiber bundle 136 enclosed in a shrink 138 and an output facet 140 at an end distal of the catheter 106. During operation, laser beam 130 can be optically received at coupling end 134 and conveyed to output facet 140 via optical fiber bundle 136. Furthermore, a portion of laser beam 130 can be reflected by output facet 140 as reflection beam 132 (dashed line as shown in FIG. 1B) and transmitted back to laser 102 via optical fiber bundle 136, coupling end 134, and catheter connector housing 122.

As outlined above, mirror 126 will not be 100% reflective. For example, mirror 126 can be 99.5% reflective. Likewise, the mirror 126 may be slightly more reflective to light having a particular polarization than to light having the opposite polarization. Accordingly, although some of reflection beam 132 will be reflected by the mirror 126 (e.g., as depicted in FIG. 1B), a portion of reflection beam 132 can be transmitted through mirror 126 and be incident on the second sensor 128b. The second sensor 128b can be arranged to measure the energy of reflection beam 132. As will be explained in greater detail below, signals from the second sensor 128b can be used to determine whether a reduction of the coupling efficiency between laser 102 and catheter 106 and/or a possible malfunction in the laser 102 itself.

Figure 1D:
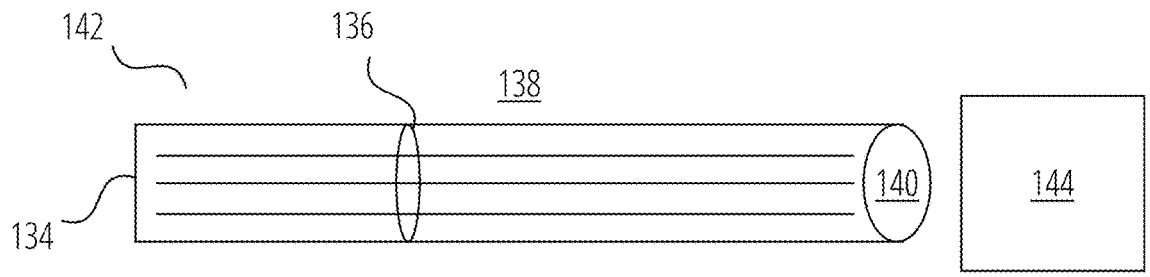
FIG. 1D illustrates a testing catheter for use with configuring the laser ablation system of FIG. 1A in accordance with embodiment(s).

FIG. 1D illustrates a testing catheter 142, in accordance with non-limiting example(s) of the present disclosure. In one embodiment, testing catheter 142 can be similar to catheter 106 with the addition of energy sensor 144. It is noted that although testing catheter 142 is depicted with a different reference number than catheter 106, this is done for purposes of clarity in description, while in practice, testing catheter 142 can be the same catheter 106 used in conjunction with the energy sensor 144. In some examples, the energy sensor 144 can be a hand held energy meter arranged to measure the amount of laser energy output from output facet 140. As noted above, the coupling end 134 of catheter 106 can include an RFID transmitter, which can be used to limit usage of catheter 106 to single use, or prevent use of laser 102 with unauthorized catheters 106. It is noted that testing catheter 142 can also include an RFID transmitter in coupling end 134. However, the RFID transmitters in testing catheter 142 may not be limited to single use. For example, processor 108 can execute instructions 116 to determine a serial number associated with testing catheter 142 (e.g., based on an RFID transmitter in the coupling end 134 of the testing catheter) and can determine that multiple uses of the testing catheter 142 are allowed. This is described in greater detail below.

Although the present disclosure describes testing catheter 142 being like catheter 106, some embodiments may provide that testing catheter 142 is different than catheter 106. For example, energy sensor 144 can be incorporated into the distal end of testing catheter 142 forming a catheter only suitable for testing or configuring a laser ablation system 100 as described herein.

Returning to FIG. 1A, laser 102 is depicted coupled to controller 104. Said differently, controller 104 is communicatively and/or operatively coupled to laser 102 such that controller 104 can send control signals, commands, or otherwise dynamically modify the operational characteristics of laser 102 (e.g., oscillator voltage settings, amplifier voltage settings, or the like) and the laser beam generated by laser 102. Controller 104 includes processor 108, memory 110, any number of input and/or output or I/O devices 112, and interconnect 114.

Controller 104 can be any of a variety of computing devices or systems. In some embodiments, controller 104 can be incorporated into and/or implemented into the same enclosure or housing as laser 102 while in other embodiments, controller 104 can be a standalone computing device (e.g., PC, tablet computing device, laptop, workstation, server, or the like) communicatively coupled to laser 102. In some embodiments, controller 104 can be accessible via a network (e.g., the Internet, an intranet, a wide area network, a virtual private network (VPN), or the like).

The processor 108 can include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 108 may include graphics processing portions and may include dedicated memory, multiple-threaded processing and/or some other parallel processing capability. In some examples, the processor 108 may be an application specific integrated circuit (ASIC) or a field programmable integrated circuit (FPGA). In some implementations, the processor 108 may be circuitry arranged to perform particular computations, such as, related to artificial intelligence (AI) or graphics. Such circuitry may be referred to as an accelerator. Processor 108 can include multiple processors, such as, for example, a central processing unit (CPU) and a graphics processing unit (GPU).

The memory 110 can include both volatile and nonvolatile memory, which are both examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), dynamic random access memory (DRAM), NAND memory, NOR memory, phase-change memory, battery-backed volatile memories, networked storage devices, and the like.

The memory 110 may include a number of memories including a main random access memory (RAM) for storage of instructions and data during program execution and a read only memory (ROM) in which read-only non-transitory instructions are stored. Memory 110 may include a file storage subsystem providing persistent (non-volatile) storage for program and data files. Memory 110 may further include removable storage systems, such as removable flash memory.

The memory 110 may be configured to store the basic programming and data constructs that provide the functionality of the disclosed processes and other embodiments thereof that fall within the scope of the present invention. Memory 110 can store instructions 116, configuration settings 118, and test readings 120. During operation, processor 108 can read instructions 116 from memory 110, and can execute the instructions 116 to implement embodiments of the present disclosure. Memory 110 may also provide a repository for storing data used by the instructions 116 or data generated by execution of the instructions 116 (e.g., configuration settings 118, test readings 120, or the like).

I/O devices 112 can be any of a variety of devices to receive input and/or provide output. For example, I/O device 112 can include, a keyboard, a mouse, a joystick, a foot pedal, a display, a touch enabled display, a haptic feedback device, an LED, or the like.

Interconnect 114 can include logic and/or features to support a communication interface. For example, interconnect 114 may include one or more interfaces that operate according to various communication protocols or standards to communicate over direct or network communication links. Direct communications may occur via use of communication protocols or standards described in one or more industry standards (including progenies and variants). For example, interconnect 114 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like. Additionally, interconnect 114 can include logic and/or features to enable communication over a variety of wired or wireless network standards. For example, interconnect 114 may be arranged to support wired communication protocols or standards, such as, Ethernet, or the like. As another example, interconnect 114 may be arranged to support wireless communication protocols or standards, such as, for example, Wi-Fi, Bluetooth, ZigBee, LTE, 5G, or the like.

Figure 2:
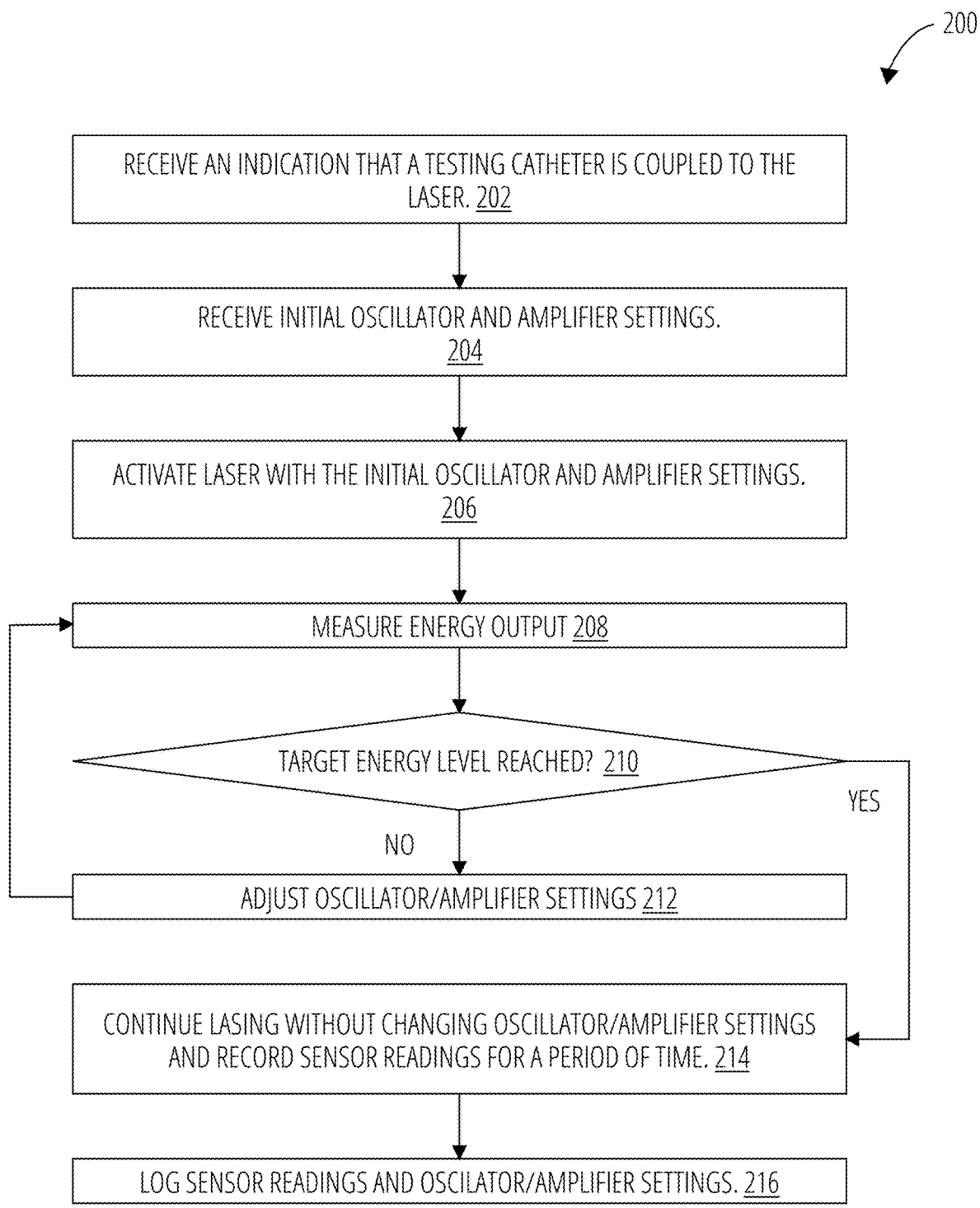
FIG. 2 illustrates a routine for configuring a laser ablation system in accordance with embodiment(s).

FIG. 2 depicts a routine 200 that may be implemented to configure or calibrate a laser ablation system, in accordance with non-limiting example(s) of the present disclosure. In some embodiments, routine 200 can be performed at a factory, for example during manufacture of laser ablation system 100. In other examples, routine 200 can be performed in the field, for example, as part of a routine service of the laser ablation system 200 or as part of a service call resulting from a malfunction of the laser ablation system 200.

Additionally, it is noted that routine 200 can be a part of a larger calibration routine (e.g., routine 300, or the like). For example, routine 200 can be performed as a subroutine within a larger configuration routine that is implemented to configure multiple power output levels of a laser ablation system and/or configure a power output level of the laser ablation system using multiple catheters. Routine 300 is described in greater detail below in conjunction with FIG. 3.

Routine 200 can be implemented to configure or calibrate laser ablation system 100, using testing catheter 142, and the disclosure uses laser ablation system 100 and testing catheter 142 to describe operation and details of routine 200. However, it is noted that routine 200 could be used with a laser ablation system and testing catheter different than laser ablation system 100 and testing catheter 142.

It is noted that in some embodiments, routine 200 can be performed one or more times. For example, routine 200 can be performed for each available power level. As another example, routine 200 can be performed more than once for each available power level and the configuration determined based on the results of the multiple iterations of routine 200. This is described in greater detail below with reference to FIG. 3.

Routine 200 can begin at block 202. At block 202 "receive an indication that a testing catheter is coupled to the laser" an indication that a testing catheter is coupled to laser 102 is received. For example, in executing instructions 116, processor 108 can receive an indication that testing catheter 142 is coupled to laser 102. As a specific example, catheter connector housing 122 can include circuitry to receive signals from a transmitter (e.g., a radio frequency identification (RFID) transmitter in coupling end 134 or the like) indicating testing catheter 142 is coupled to laser 102. With some embodiments, laser ablation system can be arranged to receive (e.g., via I/O device 112, or the like) an indication that testing catheter 142 is coupled to the laser ablation system 100. For example, with some embodiments, testing catheter 142 may not have an RFID transmitter and a user may manually indicate that a testing catheter is coupled to the laser ablation system 100. As noted above, testing catheter 142 can be like a catheter for use during an ablation procedure (e.g., catheter 106), which is used in conjunction with the energy sensor 144 (e.g., a hand held energy meter, or the like).

Continuing to block 204 "receive initial oscillator and amplifier settings" initial settings for controlling power output of the laser 102 are received. In some examples, laser 102 is a solid state laser, such as, an Nd:YAG laser controlled by an oscillator and an amplifier. The present disclosure however is applicable to other types of lasers, such as, gas lasers, diode pumped lasers, or the like. Accordingly, voltage settings for the oscillator and amplifier are provided, which control output energy for the laser 102. Processor 108 can execute instructions 116 to generate a prompt via I/O device 112 to enter values for oscillator and amplifier settings. As a specific example, laser 102 may be arranged to generate a pulsed laser beam having a number of powers (e.g., 40 Millijoules per millimeter squared (mJ/mm$^2$) to 80 mJ/mm$^2$, such as 50 mJ/mm$^2$, 60 mJ/mm$^2$, or the like). Accordingly, processor 108 can execute instructions 116 to generate a prompt to enter oscillator and amplifier settings for one of the number of power output settings. Furthermore, processor 108 can execute instructions 116 to receive the initial oscillator and amplifier settings. In some examples, settings can be received from factory default setting (e.g., stored in memory 110, received from a network storage location, or the like) or can be received from an operator or technician of laser ablation system 100 via I/O devices 112. As another example, processor 108 can execute instructions 116 to load default oscillator and amplifier settings to begin the configuration procedure or routine 200.

Continuing to block 206 "activate laser and with the initial oscillator and amplifier settings" the laser 102 can be activated with the initial oscillator and amplifier settings received at block 204. For example, processor 108 can execute instructions 116 to send a control signal to laser 102 to cause laser 102 to begin lasing with the oscillator and amplifier settings received at block 204.

Continuing to block 208 "measure energy output" the energy output from laser 102 can be measured, via testing catheter 142. For example, processor 108 can execute instructions 116 to receive signals from energy sensor 144 comprising indications of energy (or laser power) emitted by output facet 140 of testing catheter 142. With some examples, energy sensor 144 can be electrically coupled to processor 108 (e.g., via interconnect 114, or the like) while in other examples, energy sensor 144 can be wireless coupled to processor 108 (e.g., in which case interconnect 114 may be a wireless interconnect).

Continuing to decision block 210 "target energy level reached?" it is determined whether the measured output energy from laser 102 has reached a target level of energy. Processor 108, in executing instructions 116, can determine whether the energy emitted by laser 102 (e.g., as measured by energy sensor 144) is at a target energy level. For example, processor 108 can execute instructions 116 to determine whether the energy emitted by output facet 140 of testing catheter 142 (e.g., as measured by energy sensor 144) and received at block 208 is within a percentage (e.g., 1%, 2%, 2.5%, 5%, or the like) of a specified (e.g., the target) energy level. In some examples, the target energy level will be the expected energy for the output power associated with the oscillator and amplifier settings received at block 204. For example, where the oscillator and amplifier settings received at block 204 are associated with a 50 mJ/mm$^2$ power level the target energy level can be 25.5 mJ. As such, the processor 108 can execute instructions 116 to determine whether the measured energy output is approximately 25.5 mJ, (e.g., within 0.25 mJ, within 0.5 mJ, within 0.75 mJ, within 1 mJ, or the like). As another example, where the oscillator and amplifier settings received at block 204 are associated with a 60 mJ/mm$^2$ power level the target energy level can be 27.5 mJ. As such, the processor 108 can execute instructions 116 to determine whether the measured energy output is approximately 27.5 mJ (e.g., within 0.25 mJ, within 0.5 mJ, within 0.75 mJ, within 1 mJ, or the like).

From decision block 210, routine 200 can continue to block 212 or block 214. Specifically, routine 200 can continue from decision block 210 to block 212 based on a determination at decision block 210 that the target energy level has not been reached while routine 200 can continue from decision block 210 to block 214 based on a determination at decision block 210 that the target level of energy has been reached.

If the routine 200 determined that the target energy level has not been reached at block 210, then at block 212 "adjust oscillator/amplifier settings" the oscillator and/or amplifier settings can be adjusted. Processor 108 can execute instructions 116 to send a control signal to laser 102 to cause the amplifier and/or oscillator in laser 102 to be adjusted based on the measured energy output received at block 208 and the target energy level. In particular, the voltage levels (or activation voltages) for the oscillator and amplifier can be adjusted. For example, where the measured energy output is less than target the oscillator and/or amplifier can be adjusted to increase energy output from the laser 102. As another example, where the measured energy output is greater than target the oscillator and/or amplifier can be adjusted to reduce energy output from the laser 102. In some embodiments, the amplifier voltage can be adjusted prior to adjusting the oscillator voltage. In a specific example, oscillator and amplifier voltages can have 20 settings. In such an example, the amplifier voltage level can be increased first. Where the amplifier voltage reaches the highest level (e.g., level 20, or the like) then the oscillator voltage can be increased by one level and the amplifier voltage cut in half. Said differently, at block 212 if the energy level needs to be increased (e.g., based measured energy output at block 208) then the amplifier voltage level can be increased by one or alternatively where the amplifier voltage level is already at a maximum, then the oscillator voltage level can be increased by one and the amplifier voltage level can be cut in half. From block 212, routine 200 can return to block 208.

If the routine 200 determined that the target energy level has been reached at block 210, then at block 214 "continue lasing without changing oscillator/amplifier settings and record sensor readings for a period of time" control signals can be sent to the laser 102 to cause the laser 102 to continue lasing for a specified period of time while internal sensor readings (e.g., sensor 128a and/or sensor 128b) are recorded. For example, processor 108 can execute instructions 116 to cause laser 102 to continue emitting laser beam 130 for a select period of time (e.g., 30 seconds, 60 seconds, or the like) while receiving and recording indications of readings from sensors 128a and/or sensor 128b. It is noted that sensor readings may provide output indicative of energy of laser beam 130 and/or reflection beam 132. For example, sensors 128a and/or 128b can have an output between 0.1 mW and 0.9 mW. In such an example, the threshold reading levels can be anywhere within this range.

Continuing to block 216 "log sensor readings and oscillator/amplifier settings" the readings from sensors 128a, 128b, as well as the oscillator and amplifier settings can be stored in memory 110 as test readings 120. For example, processor 108 can execute instructions 116 to store measurements from sensor 128a, 128b, energy sensor 144, as well as the oscillator and amplifier settings from block 214.

Figure 3:
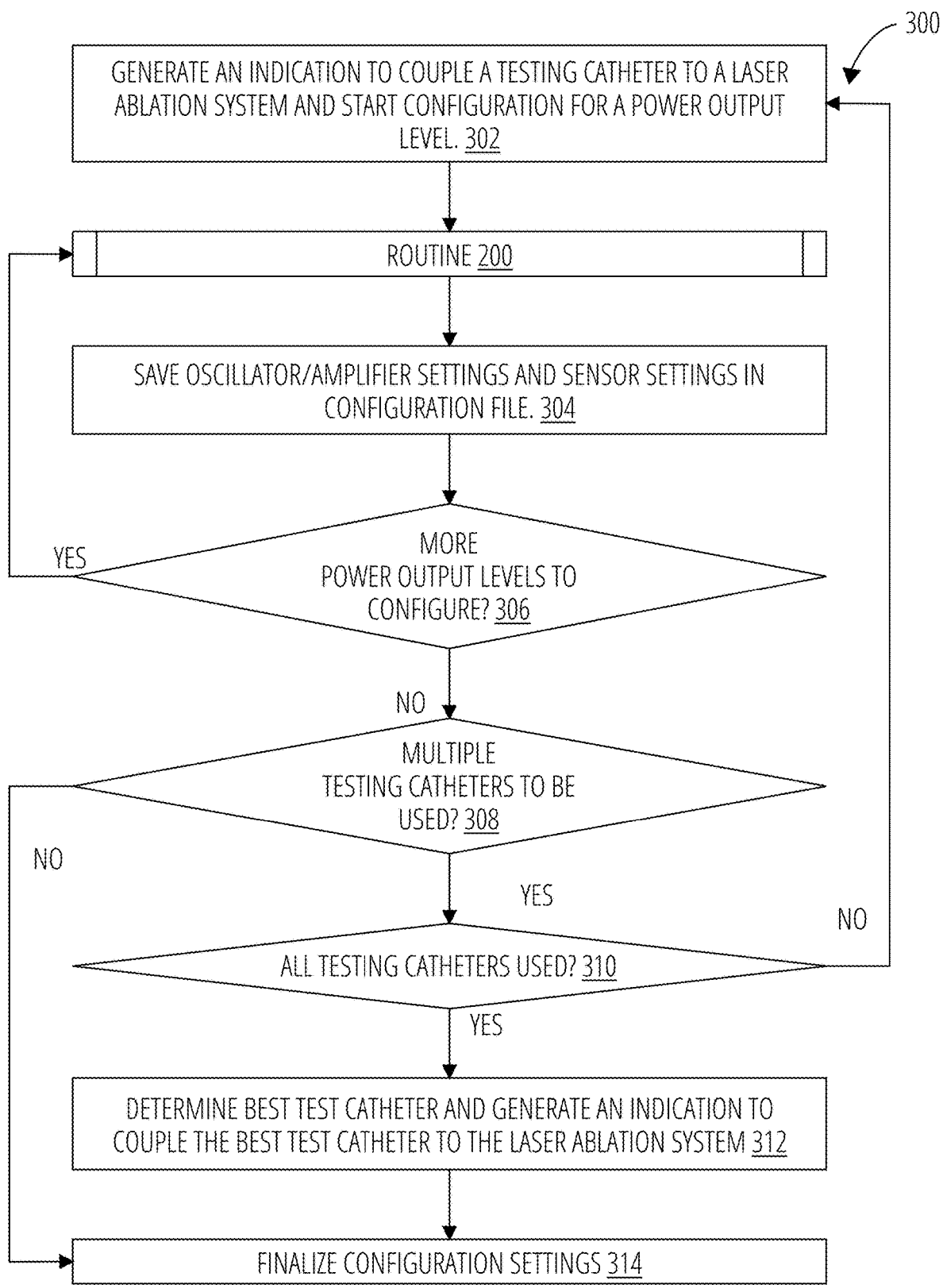
FIG. 3 illustrates another routine for configuring a laser ablation system in accordance with embodiment(s).

As noted, routine 200 can be performed multiple times. That is, routine 200 can be performed to configure the oscillator and amplifier settings and internal sensor threshold levels for multiple power output levels are within specification or desired ranges. For example, FIG. 3 illustrates a routine 300 that may be implemented to configure a laser ablation system, in accordance with non-limiting example(s) of the present disclosure. In particular, routine 300 may be implemented to configure the oscillator and amplifier settings and internal sensor threshold levels of a laser for multiple power output levels as part of (i) an overall initial set-up or configuration process of a laser ablation system (e.g., laser ablation system 100) at the time of manufacturing, or (ii) an overall maintenance process of a laser ablation system (e.g., laser ablation system 100) to ensure oscillator and amplifier settings and internal sensor thresholds levels. Routine 300 can be implemented to configure laser ablation system 100 and the disclosure uses laser ablation system 100 to describe operation and details of routine 300. However, it is noted that routine 300 could be used with a laser ablation system different than laser ablation system 100.

Routine 300 can begin at block 302. At block 302 "generate an indication to couple a testing catheter to a laser ablation system and start configuration for a power output level" an indication to couple a testing catheter to a laser ablation system to start configuration of the laser ablation system for a first power output level can be generated. For example, processor 108 can execute instructions 116 to generate an indication (e.g., graphical indication, or the like) presented via I/O device 112 (e.g., a display, or the like) comprising instructions to couple testing catheter 142 to laser ablation system 100 to start configuration of laser ablation system 100 for a first power output level.

From block 302 routine 300 can execute routine 200 (e.g., described in FIG. 2) as a subroutine. With some examples, processor 108 can execute instructions 116 to cause routine 200 to be implemented for the specific power output level (i.e., the first power output level) and can provide an indication of the initial oscillator and/or amplifier settings as well as the target energy level for use in routine 200. Upon completion of routine 200, routine 300 can continue to block 304. At block 304 "save oscillator/amplifier settings and sensor settings in configuration file" where the oscillator and amplifier settings as well as sensor readings can be saved in configuration settings 118. For example, processor 108 can execute instructions 116 to save the oscillator and amplifier settings (e.g., as adjusted set at block 206 and/or adjusted at block 212) in configuration settings 118. Furthermore, processor 108 can execute instructions 116 to save the sensors readings in configuration settings 118. In some embodiments, processor 108 can execute instructions 116 to calculate the average of the sensor readings for the period of time of block 214, to adjust for fluctuations of the energy during the time period. Said differently, processor 108 can execute instructions 116 to derive the average of the readings from sensor 126a and/or sensor 126b during the period of time of block 214.

Furthermore, processor 108 can execute instructions 116 to derive the product of the average of the sensor readings and the quotient of the target) energy level over the average of the measured emitted energy. In particular, at block 306 processor 108 can execute instructions 116 to solve the following equation: $S_{setting} = E_{target} \div E_{measured} \times Ave_{sensor}$ where $S_{setting}$ is the sensor threshold energy to be stored in configuration settings 118, $E_{target}$ is the target energy level (e.g., from decision block 210), $Ave_{Emeasured}$ is the average of the measured energy output values, and $Ave_{sensor}$ is the average of the internal sensor values. It is noted that processor 108 can execute instructions 116 to derive a sensor threshold value for both the sensor 126a and the sensor 126b.

Continuing to decision block 306 "more power output levels to configure?" a determination of whether additional power output levels are to be configured. For example, laser ablation system 100 may be provided with multiple power output levels (e.g., 50 mJ/mm$^2$ and 60 mJ/mm$^2$, or the like). In such an example, routine 300 may be iteratively performed for each of these power levels. For example, from decision block 308, routine 300 can return to subroutine 200 (e.g., to configure laser ablation system 100 for additional power output levels) or can continue to decision block 308.

At decision block 308 "multiple testing catheters to be used?" a determination of whether multiple testing catheters are to be used is made. Catheters (e.g., catheters 106, or the like) can have varying coupling efficiency with laser 102, for example, due to degradation in (e.g., due to degradation in fiber bundle 136, due to degradation of coupling end optics 134, or the like). As such, the present disclosure provides that multiple testing catheters 142 can optionally be used to provide an advantage. In particular, using multiple testing catheters as part of routine 300 can provide a more accurate result as errors resulting from a defective and/or low quality testing catheter can be factored out of the configuration and calibration.

From decision block 308, routine 300 can continue to decision block 310 or block 314. In particular, routine 300 can continue from decision block 308 to decision block 310 based on a determination that multiple testing catheters are to be used while routine 300 can continue to block 314 based on a determination that multiple testing catheters are not to be used.

At decision block 310 "all testing catheters used?" a determination of whether all testing catheters have been used is made. For example, processor 106 can execute instructions 116 to determine whether all testing catheters have been coupled to the laser system as part of routine 300. From decision block 310, routine 300 can continue to return to bock 302 or continue to block 312. In particular, routine 300 can return to block 302 from decision block 310 based on a determination that all testing catheters have not been used while routine 300 can continue to block 312 from decision block 310 based on a determination that all testing catheters have been used.

At block 312 "determine best test catheter and generate an indication to couple the best test catheter to the laser ablation system" the better of the multiple testing catheters is determined and an indication to couple the best testing catheter to the laser ablation system can be generated. The present example uses two testing catheters to clarify of descriptions, however, in practice more than two testing catheters can be used. For example, processor 108 can execute instructions 116 to determine which testing catheter 142 (e.g., had the lowest internal sensor readings. For example, the intent is to select the testing catheter 142 that is the least degraded or has the highest coupling efficiency with laser 102 so the amplifier and oscillator can be adjusted to based on the lower oscillator amplifier settings such that during an ablation procedure higher emitted energy than intended is less likely. In some embodiments one testing catheter can have lower internal sensor readings for one power output level while having higher internal sensor readings for another power output level. As a specific example, the first testing catheter 142 may have better (e.g., lower internal sensor readings) than the second testing catheter 142 for the first power output level (e.g., 50 mJ/mm$^2$) while the second testing catheter 142 may have better (e.g., lower internal sensor readings) than the first testing catheter 142 for the second power output level (e.g., 60 mJ/mm$^2$).

In such an example, processor 108 can execute instructions 116 to determine the best testing catheter 142 based on algorithm: 1. Determine the greater of these two equations| $(PL1_{one} - PL1_{two}) \times 100) \div PL1_{two}$| and $(PLZ_{one} - PL2_{two}) \times 100) \div PL2_{two}$| where $PL1_{one}$ is the sensor reading from the first catheter and first power output level, $PL1_{two}$ is the sensor reading from the second catheter and first power output level, $PL2_{one}$ is the sensor reading from the first catheter and second power output level, and $PL2_{two}$ is the sensor reading from the second catheter and second power output level; 2. Whichever output power level has the higher absolute value percentage, determine the testing catheter 142 associated with this higher absolute value percentage is the "best."

Once the "best" testing catheter 142 is determined then the processor 108 can execute instructions 116 to generate an indication (e.g., graphical indication, or the like) presented via I/O device 112 (e.g., a display, or the like) comprising instructions to couple the best testing catheter 142 (e.g., the first or the second) to laser ablation system 100. As noted above, where multiple testing catheters 142 are used, for example, to account for varying amounts of coupling efficiency between the testing catheters 142 and the laser 102, the testing catheter with the highest coupling efficiency is used. Said differently, the testing catheter 142 which reaches the target energy output with the lower internal sensor readings, indicating that the least amount of power from the laser 102 is needed to generate the target energy emission from the testing catheter 142, is used to determine oscillator and amplifier settings for a dynamic startup procedure.

From block 312, routine 300 can continue to block 314. At block 314 "finalize configuration settings" configuration settings for the laser ablation system 100 can be finalized.

For example, at block 312 processor 106 can execute instructions 118 to save the internal sensor readings as thresholds in configuration file 118. Where multiple testing catheters 142 were used the internal sensor readings associated with the best testing catheter (as outlined above) can be saved in configuration file 118 as internal sensor thresholds.

As further outlined above, some embodiments of the present disclosure provide for a dynamic startup of a laser ablation system 100. As such, oscillator and amplifier settings for this dynamic startup can be determined and/or confirmed at block 314. Where dynamic startup is not used, the oscillator and amplifier settings associated with the best (or only) testing catheter 142 can be saved in configuration file 118 to be used as starting oscillator and amplifier settings during an ablation procedure.

Where dynamic startup is used, block 314 can further include operations to determine the oscillator and amplifier settings for this dynamic startup. For example, where multiple testing catheters 142 were used as outlined above processor 108 can execute instructions 116 to initiate lasing once it is confirmed (e.g., via RFID, or the like) that the best testing catheter 142 is coupled to laser ablation system 100. Where only one testing catheter was used as outlined above, processor 108 can execute instructions 116 to initiate lasing once it is confirmed that this testing catheter 142 is coupled to the laser ablation system.

Once lasing starts the amplifier and oscillator can be adjusted until a dynamic startup target power level, as measured by energy sensor 144, is reached. In particular, the dynamic startup target power level can be a percentage of the target power level (e.g., 98%, 95,%, 90%, or the like). As a specific example, the dynamic startup target power levels can be 24.0 mJ+/−1.0 mJ for 50 mJ/mm$^2$ power output level and 26.0 mJ+/−1.0 mJ for 60 mJ/mm$^2$ power output level. At block 312, processor 106 can execute instructions 116 to cause the oscillator and amplifier settings of the laser 102 to be adjusted until the measured output from the testing catheter 142 is (or is approximately) the dynamic startup target power level. The oscillator and amplifier settings associated with the dynamic startup target power level can be saved in configuration file 118 as the starting oscillator and amplifier settings for the various power levels.

It is noted that the energy output from catheter 106 does not have a linear relationship to the oscillator and amplifier settings of the laser 102. As such, the initial oscillator and amplifier settings for dynamic startup control as outlined herein are determined during configuration (e.g., routine 300) as opposed to being set as a percentage of oscillator and amplifier settings associated with actual target power output.

As an alternative embodiment, processor 106 can execute instructions 116 to save both dynamic startup oscillator and amplifier settings as well as non-dynamic startup oscillator and amplifier settings. As such, during operation, a user (e.g., physician, or the like) can determine whether to start the laser ablation system with or without the dynamic startup control features discussed herein (e.g., refer to FIG. 4).

After completion of routine 300, configuration settings 118 can include an indication of the oscillator and amplifier settings for all power output levels as well as the internal sensor threshold energy levels (e.g., for sensor 128a (in cases where 100 only includes sensor 128a), sensor 128b, or both sensor 128a and 128b) for all power levels.

Figure 4:
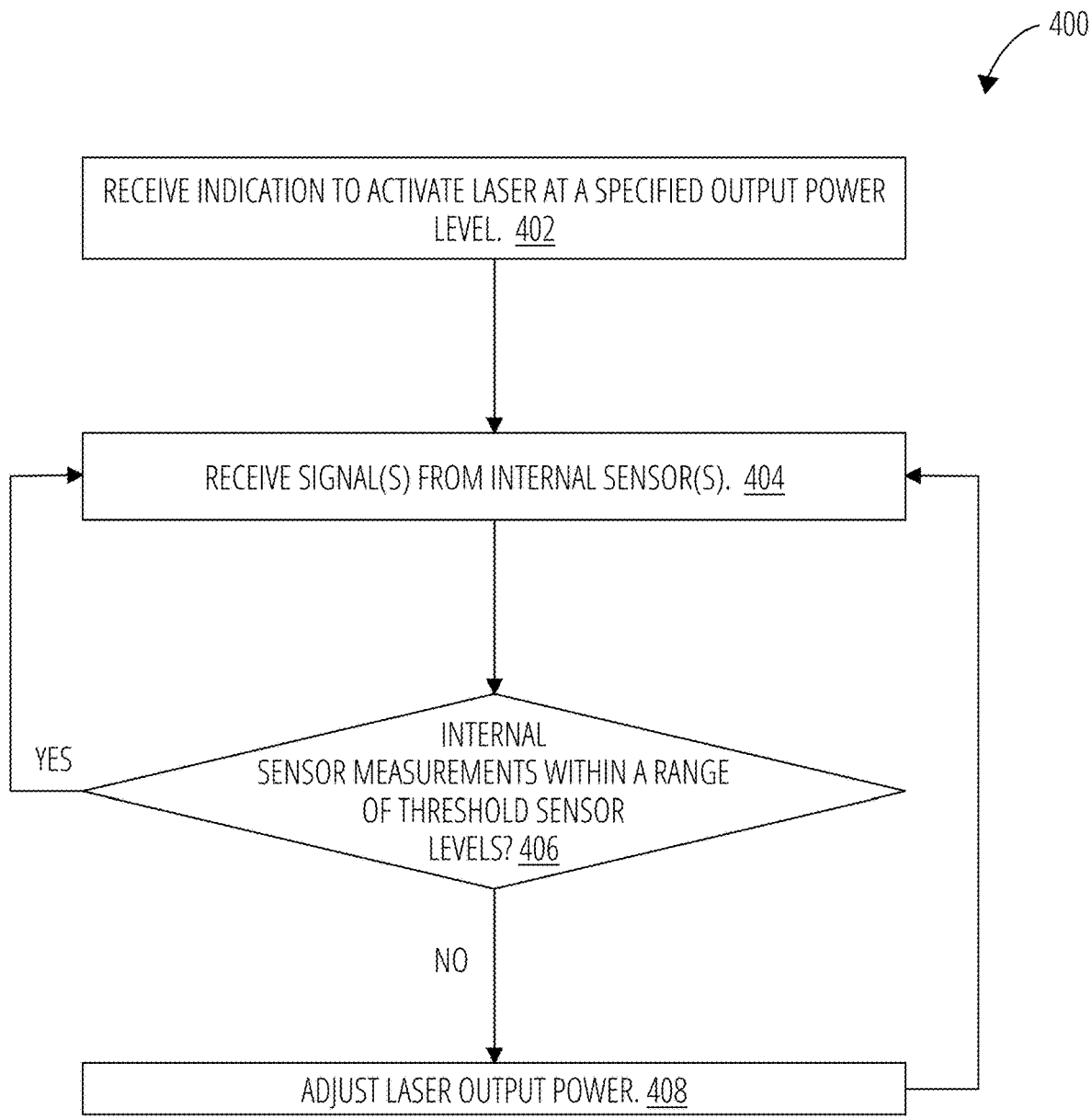
FIG. 4 illustrates a routine for dynamically controlling a laser ablation system at startup in accordance with embodiment(s).

FIG. 4 depicts a routine 400 that may be implemented to provide a dynamic power control, during initiation or starting of a laser ablation system 100 or during continued operation of a laser ablation system 100, in accordance with non-limiting example(s) of the present disclosure. Routine 400 can be implemented to dynamically ramp up power output for laser ablation system 100 and the disclosure uses laser ablation system 100 to describe operation and details of routine 400. Likewise, routine 400 can be implemented to dynamically control power output during use of a laser ablation system (e.g., during a laser ablation procedure, or the like). However, it is noted that routine 400 could be used with a laser ablation system different than laser ablation system 100.

Routine 400 can begin at block 402. At block 402 "receive an indication to activate a laser at a specified output power" an indication to activate a laser 102 at a specified output power is received. For example, laser ablation system 100 may be arranged to emit laser energy at one of a variety of levels. Accordingly, at block 402, processor 108 can execute instructions 116 to receive an indication of a power output level (e.g., 50 mJ/mm$^2$, 60 mJ/mm$^2$, or the like). Additionally, with some embodiments, laser ablation system 100 can be equipped with a foot pedal activation switch or other type of laser activation switch. Accordingly, at block 402 processor 108 can further execute instructions 116 to receive a control signal from an activation switch (e.g., a foot pedal, or the like).

As outlined above, for example in detail with respect to routine 300 and FIG. 3, initial oscillator and amplifier settings are determined during configuration of the laser ablation system 100. With some embodiments, the initial oscillator and amplifier settings are determined to provide an output energy from the catheter 106 (e.g., the dynamic startup target power output) that is an amount less than the actual desired output energy (e.g, the target power output). It is noted that the oscillator and amplifier settings stored in configuration file 118 can correspond to oscillator and amplifier settings for this dynamic startup or not, as outlined above. As such, in some examples, at block 402, processor 106 can execute instructions 116 to receive an indication to active the laser using dynamic startup control and can set the initial oscillator and amplifier settings using the dynamic startup oscillator and amplifier settings from configuration file 118. As noted, in some embodiments the dynamic startup control is an optional feature, and in such examples, processor 106 can execute instructions 116 to receive an indication to active the laser using non-dynamic startup control and can set the initial oscillator and amplifier settings using the non-dynamic startup oscillator and amplifier settings from configuration file 118.

It is to be appreciated that starting with a lower than called for output power level provides that uncontrolled common high energy pulses in the first few seconds of lasing, which may induce a severe damage to the optical fiber bundle 136 of catheter 106, may be avoided.

Continuing to block 404 "receive signal from internal sensor(s)" signals from the internal sensor(s) can be received. For example, processor 108 can execute instructions 116 to receive signals from sensor 128a comprising an indication of the energy or power output from laser beam 130. Furthermore, where both sensor 128a and sensor 128b are used, processor 108 can execute instructions 116 to receive signals from sensor 128b comprising indications of the reflection beam 132.

Continuing to decision block 406 "internal sensor measurements within a range of threshold sensor levels?" a determination of whether the measurements from the internal sensor(s) are within a range of the threshold sensor levels determined during configuration of the laser ablation system 100 and stored in configuration file 118. For example, as outlined above, threshold sensor levels (measurements) for specified output powers are determined during configuration of the laser ablation system 100 as described above with respect to FIG. 2 and FIG. 3. As such, at decision block 406 a determination can be made as to whether the measurements from internal sensor(s) are within a range (e.g., +/−0.1 W, +/−0.02 W, +/−5%, +/−2%, or the like) of the thresholds for sensor 128*a* and/or 128*b* stored in configuration settings 118 associated with the output power level.

From decision block 406, routine 400 can continue to block 408 or can return to block 404. At block 408 "adjust laser output power" the output power of the laser can be adjusted and the routine 400 can return to block 404. For example, processor 108 can execute instructions 116 to increase the oscillator and/or amplifier settings. For example, where a determination at block 406 is made that the internal sensor measurements are not within a range of the threshold sensor levels then the oscillator and/or amplifier settings can be adjusted accordingly. For example, if the internal sensor measurements are higher than the thresholds then the amplifier voltage can be reduced by 1 voltage level. As another example, where the internal sensor measurements are lower than the thresholds then the amplifier voltage can be increased by 1 voltage level. As another example, where the internal sensor measurements are higher (or lower) than the thresholds by a larger margin (e.g., 5% difference from thresholds, or the like) the amplifier voltage can be reduced (or increased) by more than 1 voltage level (e.g., by 3 voltage levels, or the like). Furthermore, where the amplifier voltage level is already as the maximum (or minimum) the oscillator settings and amplifier voltage levels can be adjusted in parallel. For example, the amplifier voltage level can be set at half the maximum voltage and the oscillator settings either increased or decreased by 1 voltage level, depending upon whether the measurement from the internal sensor 128*a* is greater than or less than the threshold level.

It is noted, that oscillator and amplifier voltage levels may have a low voltage (e.g., 400V) and a high voltage (e.g., 500V) and the range between the low voltage and the high voltage can be split into "levels," for example 20 levels. Using the example above where the range is 100V wide and split into 20 levels, each increase would increase the voltage applied to the oscillator and/or amplifier by 5 V. Examples, however, are not limited in this context.

Accordingly, routine 400 provides for dynamic control of a laser ablation system. As noted above, with some embodiments, the system is configured with an initial startup period in which the initial oscillator and amplifier settings are purposefully set to produce emitted laser energy below the target laser energy while the laser ablation system is dynamically adjusted until the desired target laser energy level is reached, often within the first few seconds of laser delivery. As such, reduction in fluctuations of emitted energy can be provided during this initial startup period to reduce potential damage to the optical fiber bundle 136 of catheter 106. Furthermore, in some embodiments, delivery of therapeutic energy to tissue can begin sooner than otherwise might be possible. Further still, dynamic control of the laser ablation system during operation is provided in combination with, or upon completion of, the initial startup period.

Figure 5:
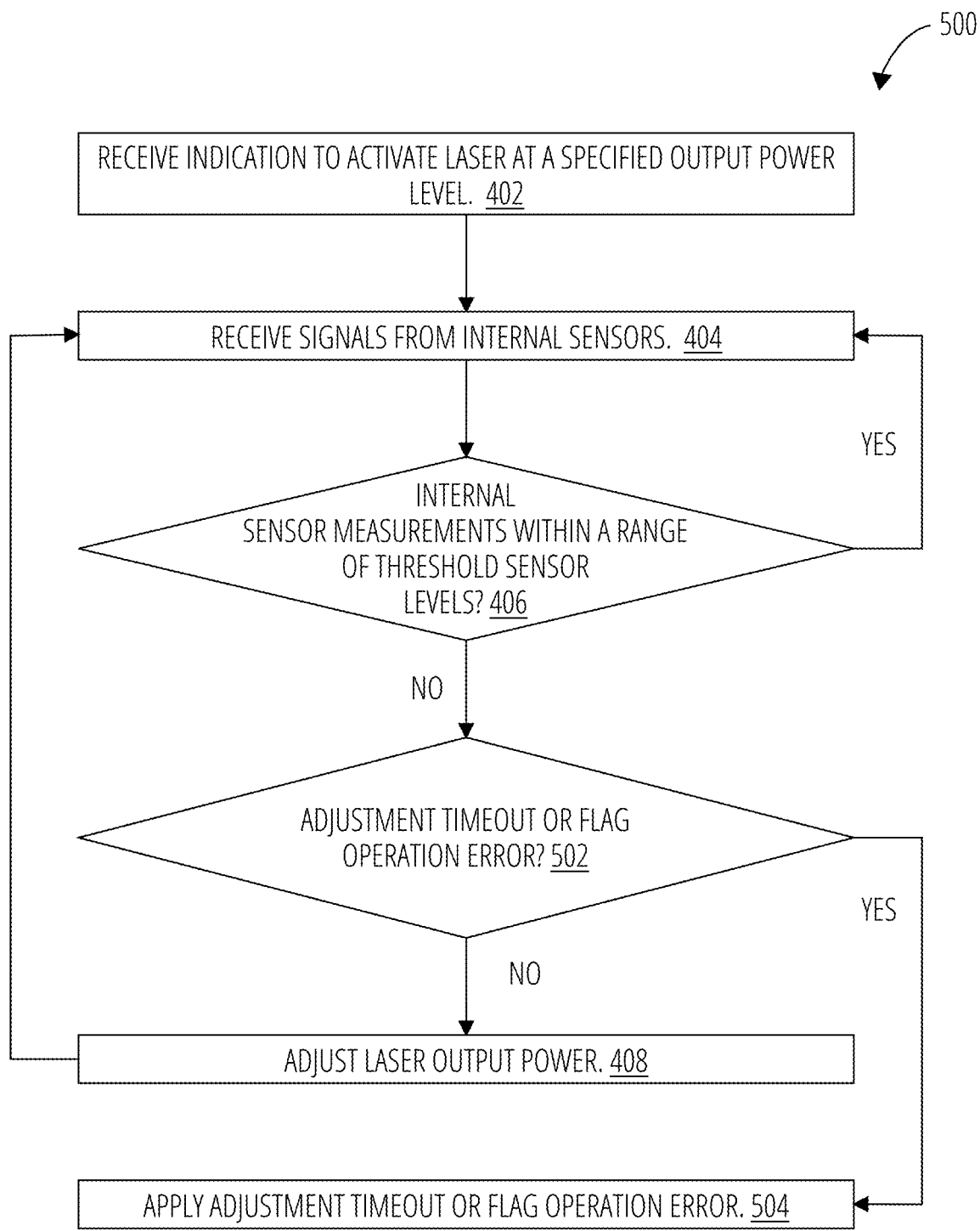
FIG. 5 illustrates a routine for dynamically controlling a laser ablation system during operation in accordance with embodiment(s).

FIG. 5 depicts a routine 500 that may be implemented to provide dynamic power control during startup and/or operation of a laser ablation system 100, in accordance with non-limiting example(s) of the present disclosure. Routine 500 can be implemented to dynamically control power output for laser ablation system 100 and the disclosure uses laser ablation system 100 to describe operation and details of routine 500. However, it is noted that routine 500 could be used with a laser ablation system different than laser ablation system 100. It is noted that routine 500 differs from routine 400 in that routine 500 provides some optional error checking not described with respect to routine 400 and FIG. 4. However, routine 500 does make reference to blocks of routine 400 and FIG. 4. This is not intended to be limiting.

Routine 500 can begin at block 402, continue to block 404, and further continue to decision block 406. From decision block 406, routine 500 can return to block 404 or continue to decision block 502. Routine 500 can return to block 404 from decision block 406 where a determination at decision block 406 is made that the internal sensor measurements are within a range of the threshold sensor levels while routine 500 can continue from decision block 406 to decision block 502 based on a determination that the internal sensor measurements are not within a range of the threshold sensor levels.

At decision block 502 "adjustment timeout out flag operation error" a determination of whether to pause dynamic adjustment of power output or to flag another possible error is made. For example, some embodiments can include periodic time outs to adjusting the output power. For example, processor 108 can execute instructions 116 to determine (e.g., at decision block 502) that a limit to the amount the amplifier and/or oscillator voltage levels can be adjusted has been reached (e.g., in a period of time or an absolute maximum of adjustments). In other embodiments, processor 108 can execute instructions 116 to determine whether a difference in sensor 128*a* and sensor 128*b* is detected. For example, where signals from sensor 128*a* indicate that the power level of laser beam 130 is stable but signals from sensor 128*b* indicate that the power level of reflection beam 132 is unstable, an error or malfunction with the laser 102 may be present. As such, processor 108 can execute instructions 116 to determine that an error should be flagged. With further or alternative embodiments, processor 108 can execute instructions 116 to determine whether a change of more than an absolute amount (e.g., 15%, 20%, 25%, or the like) of the oscillator and/or amplifier voltage levels an error can be generated. In still further or alternative embodiments, processor 108 can execute instructions 116 to determine whether a change of the sensor readings of more than an absolute amount (e.g., 15%, 20%, 25% or the like) and can trigger an error and/or stop the ablation procedure if the maximum change is exceeded.

From decision block 502, routine 500 can continue to block 408 or block 504. For example, routine 500 can continue from decision block 502 to block 504 based a determination at decision block 502 that adjustments should be paused or an error should be flagged while routine 500 can continue from decision block 502 to block 408 based a determination at decision block 508 that adjustments should not be paused or an error should not be flagged.

At block 504 "apply adjustment timeout or flag operation error" the dynamic adjustment of output power can be paused or an operation error can be flagged. For example, processor 108 can execute instructions 116 to pause routine 500 and resume routine 500 after a set amount of time has elapsed. As another example, processor 108 can execute instructions 116 to generate a notification (e.g., graphical indication of the error presented on I/O device 112, or the like) and can terminate the ablation procedure.

Accordingly, as outlined above, routines 400 and 500 provide for a significantly more stable output power of the laser beam than using conventional techniques.

Figure 6A:
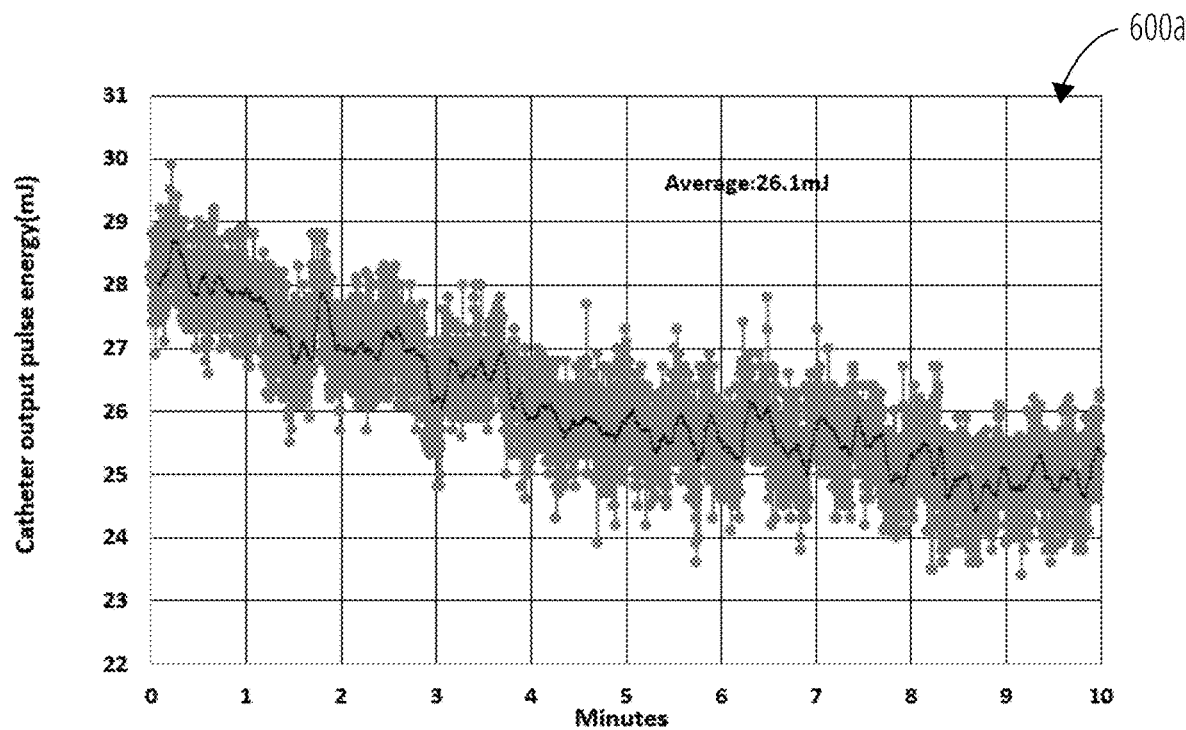
FIG. 6A illustrates a plot.

FIG. 6A illustrates a plot 600a depicting catheter output pulse energy (in mJ) on the Y axis and time (in minutes) on the X axis for a laser ablation system 100 output at a 60 mJ/mm$^2$ power output level with a room temperature between 19.0 and 19.5 degrees Celsius without using the dynamic startup control and stability corrections of routine 400 and routine 500. As can be seen there is a wide fluctuation in the measured output power (e.g., Y axis) and the average output power is 26.1 mJ. Further, it is evident from plot 600a in FIG. 6A that the energy emitted degrades over time. The impact of such a wide fluctuation in the measured output power and the overage output power on an ablation procedure is that the laser beam output pulse energy does not remain at the necessary power threshold for a required period of time needed to achieve desired ablation thresholds. Said differently, such a wide fluctuation in the measured output power and the overage output power on an ablation procedure can result in (an inadequate) output pulse energy that fails to achieve the desired results of the ablation procedure.

Figure 6B:
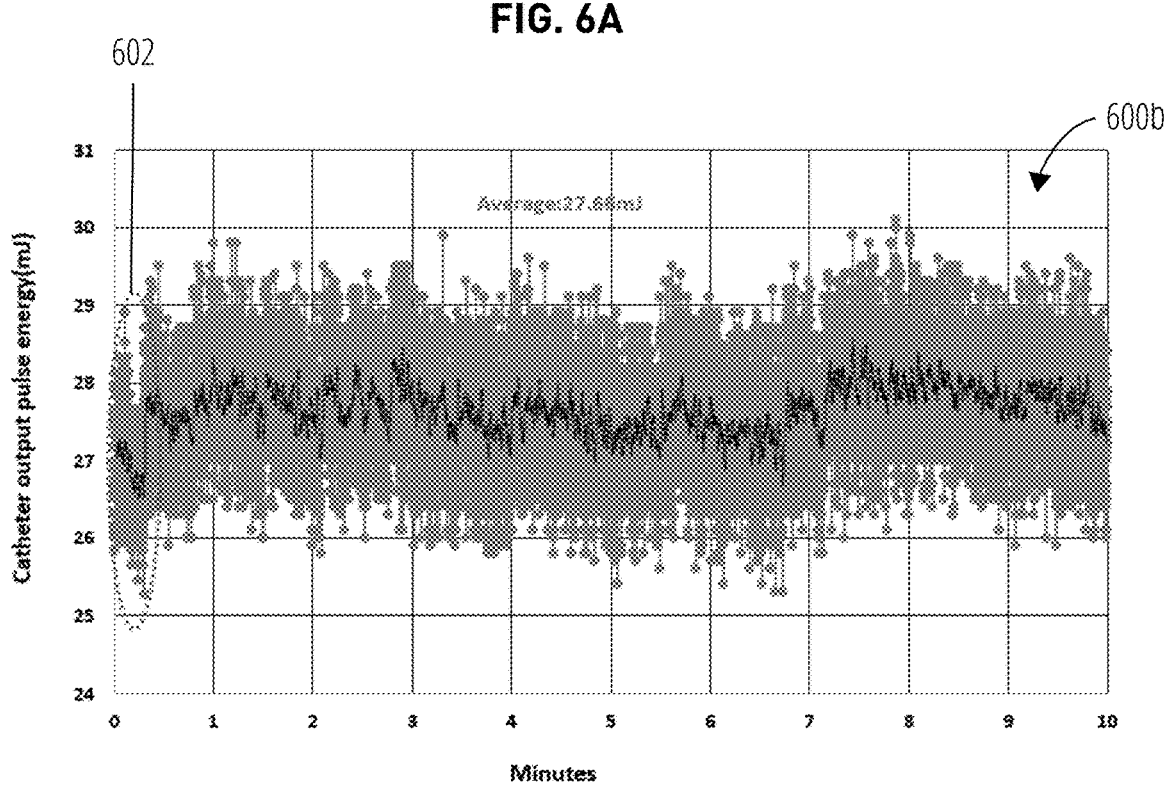
FIG. 6B illustrates another plot.

FIG. 6B illustrates a plot 600b depicting catheter output pulse energy (in mJ) on the Y axis and time (in minutes) on the X axis for a laser ablation system 100 output at a 60 mJ/mm$^2$ power output level with a room temperature between 19.0 and 19.5 degrees Celsius while using the dynamic start and stability corrections of routine 400 and routine 500. As can be seen the output power (e.g., Y axis) is significantly more stable than without the dynamic control routines of the present disclosure (e.g., versus FIG. 6A). The average power output while using the dynamic control of the present disclosure is further increased (versus without) to 27.6 mJ. It is further evident from plot 600b that the stability, or rather lack of fluctuations in power output, is significantly improved when using the dynamic startup and control procedures of the present disclosure. For example, power quickly ramps up to the specified power output using the dynamic startup of routines 400 and/or 500 as evidence by the output power indicated by period 602. The power output while using the dynamic control of the present disclosure is advantageous because it reduces the fluctuations or changes in emitted energy, resulting from stabilization of the laser, changes in operating environment temperature, or the like.

Figure 7:
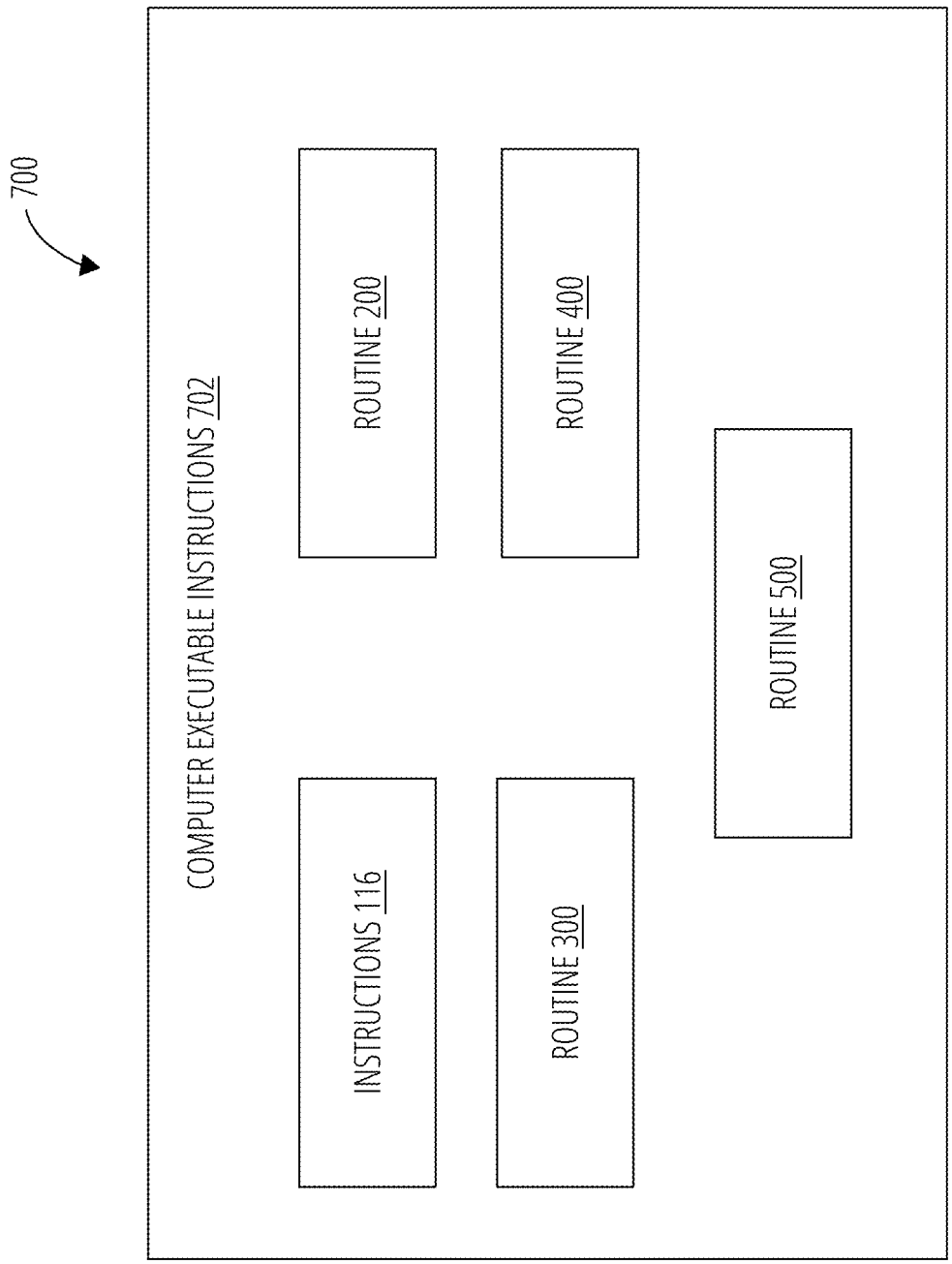
FIG. 7 illustrates a computer-readable storage medium 700 in accordance with embodiment(s).

FIG. 7 illustrates computer-readable storage medium 700. Computer-readable storage medium 700 may comprise any non-transitory computer-readable storage medium or machine-readable storage medium, such as an optical, magnetic or semiconductor storage medium. In various embodiments, computer-readable storage medium 700 may comprise an article of manufacture. In some embodiments, 700 may store computer executable instructions 702 with which circuitry (e.g., processor 108, or the like) can execute. For example, computer executable instructions 702 can include instructions to implement operations described with respect to instructions 116, routine 200, routine 300, routine 400 and/or routine 500. Examples of computer-readable storage medium 700 or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions 702 may include any suitable type of code, such as source code, compiled code, interpreted code, executable code, static code, dynamic code, object-oriented code, visual code, and the like.

Figure 8:
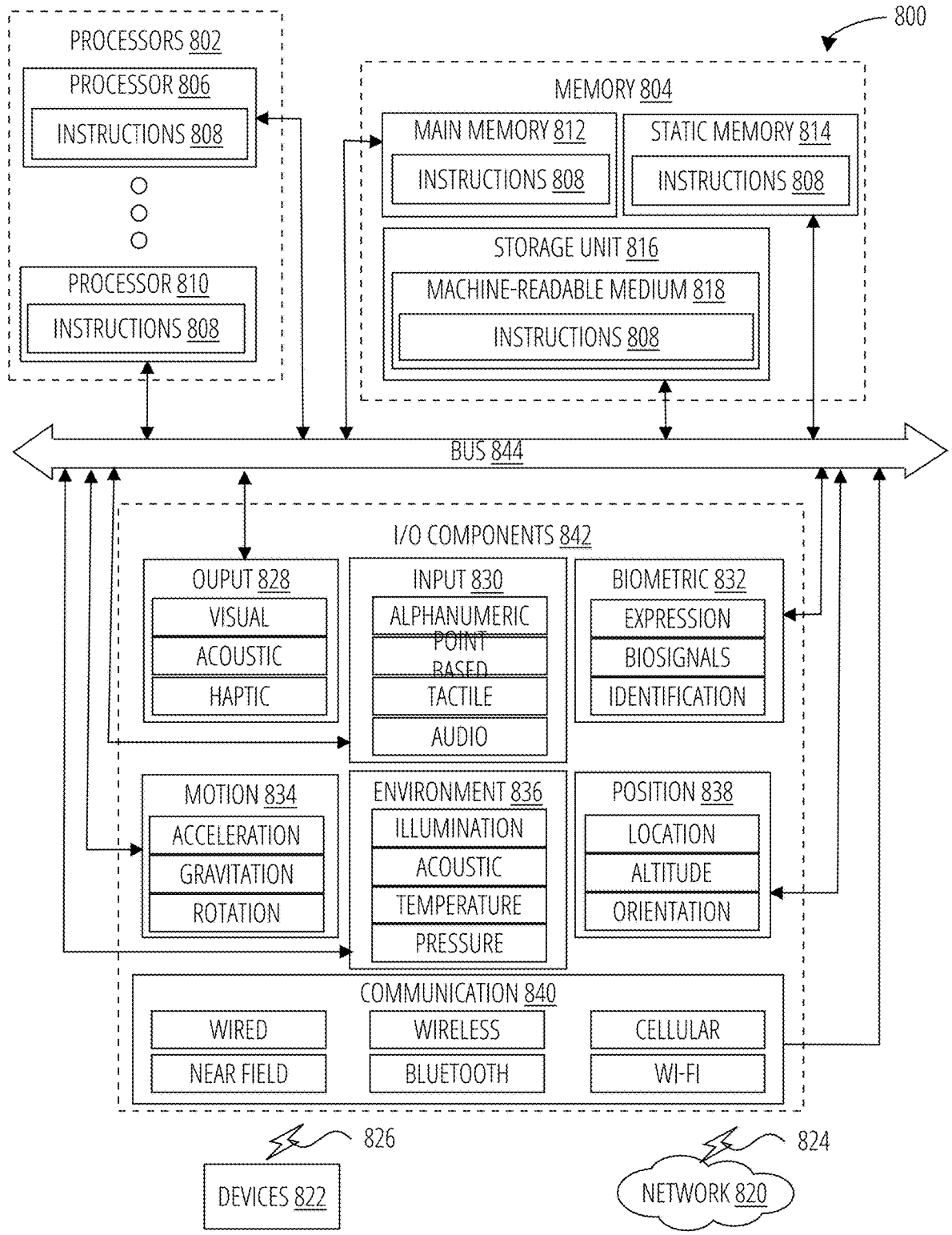
FIG. 8 illustrates a diagrammatic representation of a machine 800 in the form of a computer system in accordance with embodiment(s).

FIG. 8 illustrates a diagrammatic representation of a machine 800 in the form of a computer system within which a set of instructions may be executed for causing the machine to perform any one or more of the methodologies discussed herein. More specifically, FIG. 8 shows a diagrammatic representation of the machine 800 in the example form of a computer system, within which instructions 808 (e.g., software, a program, an application, an applet, an app, or other executable code) for causing the machine 800 to perform any one or more of the methodologies discussed herein may be executed. For example, the instructions 808 may cause the machine 800 to execute instructions 116 of FIG. 1A, routine 200 of FIG. 2, routine 300 of FIG. 3, routine 400 of FIG. 4, routine 500 of FIG. 5, or the like. More generally, the instructions 808 may cause the machine 800 to configure a laser ablation system 100 and/or dynamically control power during startup or operation of laser ablation system 100.

The instructions 808 transform the general, non-programmed machine 800 into a particular machine 800 programmed to carry out the described and illustrated functions in a specific manner. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 808, sequentially or otherwise, that specify actions to be taken by the machine 800. Further, while only a single machine 800 is illustrated, the term "machine" shall also be taken to include a collection of machines 200 that individually or jointly execute the instructions 808 to perform any one or more of the methodologies discussed herein.

The machine 800 may include processors 802, memory 804, and I/O components 842, which may be configured to communicate with each other such as via a bus 844. In an example embodiment, the processors 802 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 806 and a processor 810 that may execute the instructions 808. The term "processor" is intended to include multi-core processors that may comprise two or more independent processors (sometimes referred to as "cores") that may execute instructions contemporaneously. Although FIG. 8 shows multiple processors 802, the machine 800 may include a single processor with a single core, a single processor with multiple cores (e.g., a multi-core processor), multiple processors with a single core, multiple processors with multiples cores, or any combination thereof.

The memory 804 may include a main memory 812, a static memory 814, and a storage unit 816, both accessible to the processors 802 such as via the bus 844. The main memory 804, the static memory 814, and storage unit 816 store the instructions 808 embodying any one or more of the methodologies or functions described herein. The instructions 808 may also reside, completely or partially, within the main memory 812, within the static memory 814, within machine-readable medium 818 within the storage unit 816, within at least one of the processors 802 (e.g., within the processor's cache memory), or any suitable combination thereof, during execution thereof by the machine 800.

The I/O components 842 may include a wide variety of components to receive input, provide output, produce output, transmit information, exchange information, capture measurements, and so on. The specific I/O components 842 that are included in a particular machine will depend on the type of machine. For example, portable machines such as mobile phones will likely include a touch input device or other such input mechanisms, while a headless server machine will likely not include such a touch input device. It will be appreciated that the I/O components 842 may include many other components that are not shown in FIG. 8. The I/O components 842 are grouped according to functionality merely for simplifying the following discussion and the grouping is in no way limiting. In various example embodiments, the I/O components 842 may include output components 828 and input components 830. The output components 828 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 830 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 842 may include biometric components 832, motion components 834, environmental components 836, or position components 838, among a wide array of other components. For example, the biometric components 832 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 842 may include communication components 840 operable to couple the machine 800 to a network 820 or devices 822 via a coupling 824 and a coupling 826, respectively. For example, the communication components 840 may include a network interface component or another suitable device to interface with the network 820. In further examples, the communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 822 may be another machine or any of a wide variety of peripheral devices (e.g., a peripheral device coupled via a USB).

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geolocation, location via Wi-Fi® signal triangulation, location via detecting an NFC beacon signal that may indicate a particular location, and so forth.

The various memories (i.e., memory 804, main memory 812, static memory 814, and/or memory of the processors 802) and/or storage unit 816 may store one or more sets of instructions and data structures (e.g., software) embodying or utilized by any one or more of the methodologies or functions described herein. These instructions (e.g., the instructions 808), when executed by processors 802, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 820 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 820 or a portion of the network 820 may include a wireless or cellular network, and the coupling 824 may be a Code Division Multiple Access (CDMA) connection, a Global System for Mobile communications (GSM) connection, or another type of cellular or wireless coupling. In this example, the coupling 824 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 808 may be transmitted or received over the network 820 using a transmission medium via a network interface device (e.g., a network interface component included in the communication components 840) and utilizing any one of a number of well-known transfer protocols (e.g., hypertext transfer protocol (HTTP)). Similarly, the instructions 808 may be transmitted or received using a transmission medium via the coupling 826 (e.g., a peer-to-peer coupling) to the devices 822. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 808 for execution by the machine 800, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Terms used herein should be accorded their ordinary meaning in the relevant arts, or the meaning indicated by their use in context, but if an express definition is provided, that meaning controls.

Herein, references to "one embodiment," "an embodiment," "one example," "an example, or "embodiments" and "examples" in the plural do not necessarily refer to the same embodiment or require plural embodiments, although it may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

By using genuine models of anatomy more accurate surgical plans may be developed than through statistical modeling.

What is claimed is:

1. A method of controlling a laser ablation system, the method comprising:
   receiving, at a controller of the laser ablation system, an indication to activate the laser ablation system at a power output level chosen from a plurality of power output levels, the laser ablation system comprising a first internal sensor configured to measure, before an output of the laser ablation system, an energy of at least a portion of a laser beam generated within the laser ablation system, wherein each power output level of the plurality of power output levels has an associated set of configuration settings that is preconfigured and that results in the laser ablation system being activated in a start-up period at a respective power output level that is less than the chosen power output level;
   sending during the start-up period, from the controller, a control signal to activate the laser ablation system using the associated set of configuration settings for the chosen power output level, wherein using the associated set of configuration settings results in the laser ablation system being activated in the start-up period at the respective power output level that is less than the chosen power output level; and
   based on activating the laser ablation system, iteratively (i) receiving a sensor output from the first internal sensor and (ii) adjusting at least one setting of the associated set of configuration settings in the start-up period based in-part on the sensor output from the first internal sensor and a threshold sensor level that is associated with the chosen power output level, the at least one setting being at least one of an oscillator setting of the laser ablation system or an amplifier setting of the laser ablation system, wherein the iteratively (i) receiving and (ii) adjusting in the start-up period dynamically adjust power output of the laser ablation system, and wherein the dynamically adjusting is from the respective power output level, that is less than the chosen power output level, towards the chosen power output level.

2. The method of claim 1, wherein the associated set of configuration settings comprise a voltage level chosen from a plurality of voltage levels for an amplifier and a voltage level chosen from a plurality of voltage levels for an oscillator of the laser ablation system, and wherein adjusting the at least one setting based on the sensor output from the first internal sensor and the threshold sensor level comprises:
   determining whether the sensor output from the first internal sensor is less than the threshold sensor level;
   responsive to a determination that the sensor output from the first internal sensor is less than the threshold sensor level:
   increasing the voltage level for the amplifier, or decreasing the voltage level for the amplifier and increasing the voltage level for the oscillator,
determining whether the sensor output from the first internal t sensor is greater than the threshold sensor level; and
responsive to a determination that the sensor output from the first internal sensor is greater than the threshold sensor level:
  decreasing the voltage level for the amplifier, or
  increasing the voltage level for the amplifier and decreasing the voltage level for the oscillator.

3. The method of claim 2, wherein determining whether the sensor output from the first internal sensor is less than the threshold sensor level comprises:
  determining whether the sensor output from the first internal sensor is less than or equal to a result of the threshold sensor level minus a first range;
  determining whether the sensor output from the first internal sensor is less than or equal to a result of the threshold sensor level minus a second range based on a determination that the sensor output of the first internal sensor is less than or equal to the result of the threshold sensor level minus the first range, wherein the second range is greater than the first range.

4. The method of claim 3, wherein determining whether the sensor output from the first internal sensor is greater than the threshold sensor level comprises:
  determining whether the sensor output from the first internal sensor is greater than or equal to a result of the threshold sensor level plus the first range;
  determining whether the sensor output from the first internal sensor is greater than or equal to a result of the threshold sensor level plus the second range based on a determination that the sensor output of the first internal sensor is greater than or equal to the result of the threshold sensor level plus the first range.

5. The method of claim 1, wherein the laser ablation system comprises a second internal sensor, the second internal sensor being an internal reflection beam sensor configured to measure an energy of at least a portion of a reflection of the laser beam from a catheter optically coupled to the laser ablation system, and wherein the method further comprises:
  receiving a sensor output from the internal reflection beam sensor; and
  determining whether the sensor output from the internal reflection beam sensor is greater than a threshold reflection beam level or less than the threshold reflection beam level.

6. The method of claim 5, further comprising sending, from the controller, a second control signal to deactivate the laser ablation system based on the determination that the sensor output from the internal reflection beam sensor is greater than the threshold reflection beam level or less than the threshold reflection beam level.

7. The method of claim 1, wherein the power output level is substantially equal to a target power, and wherein the threshold sensor level is associated with a power substantially equal to the target power.

8. The method of claim 5, further comprising generating an indication of an internal malfunction of the laser ablation system based on a determination that the sensor output from the internal reflection beam sensor in greater than the threshold reflection beam level or less than the threshold reflection beam level.

9. The method of claim 3, wherein increasing the voltage level for the amplifier comprises:
  increasing the voltage level for the amplifier by one (1) voltage level of the plurality of voltage levels based on (i) a determination that the sensor output of the first internal sensor is less than or equal to the result of the threshold sensor level minus the first range and (ii) a determination that the sensor output from the first internal sensor is not less than or equal to the result of the threshold sensor level minus the second range, or
  increasing the voltage level for the amplifier by more than one (1) voltage level of the plurality of voltage levels based on a determination that the sensor output from the first internal sensor is less than or equal to the result of the threshold sensor level minus the second range, and
  wherein decreasing the voltage level for the amplifier and increasing the voltage level for the oscillator comprises decreasing the voltage level for the amplifier by more than one (1) voltage level of the plurality of voltage levels and increasing the voltage level of the oscillator by one (1) voltage level of the plurality of voltage levels.

10. The method of claim 4, wherein decreasing the voltage level for the amplifier comprises:
  decreasing the voltage level for the amplifier by one (1) voltage level of the plurality of voltage levels based on (i) a determination that the sensor output from the first internal sensor is greater than or equal to the result of the threshold sensor level plus the first range and (ii) a determination that the sensor output from the first internal sensor is not greater than or equal to the result of the threshold sensor level plus the second range, or
  decreasing the voltage level for the amplifier by more than one (1) voltage level of the plurality of voltage levels based on a determination that the sensor output from the first internal sensor is greater than or equal to the combination of the threshold sensor level plus the second range, and
  wherein increasing the voltage level for the amplifier and decreasing the voltage level for the oscillator comprises increasing the voltage level for the amplifier by more than one (1) voltage level of the plurality of voltage levels and decreasing the voltage level of the oscillator by one (1) voltage level of the plurality of voltage levels.

11. The method of claim 1, wherein the power output level is between 40 mili-Jules per millimeter squared ($mJ/mm^2$) and 80 $mJ/mm^2$.

12. A method of controlling a laser ablation system, wherein the laser ablation system includes a laser and a catheter configured to be operatively coupled the laser, the method comprising:
  receiving, at a controller of the laser ablation system, an indication to activate the laser ablation system at a power output level chosen from a plurality of power output levels, the laser comprising a first internal sensor configured to measure an energy of at least a portion of a laser beam generated by the laser, wherein the portion of the laser beam measured by the first internal sensor includes a portion of the laser beam within the laser and before being transmitted to the catheter, wherein each power output level of the plurality of power output levels has an associated set of configuration settings that is preconfigured and that results in the laser ablation system being activated in a start-up period at a respective power output level that is less than the chosen power output level;

sending during the start-up period, from the controller, a control signal to activate the laser ablation system using the associated set of configuration settings for the chosen power output level, wherein using the associated set of configuration settings results in the laser ablation system being activated in the start-up period at the respective power output level that is less than the chosen power output level; and based on activating the laser ablation system, iteratively (i) receiving a sensor output from the first internal sensor and (ii) adjusting at least one setting of the associated set of configuration settings in the start-up period based in-part on the sensor output from the first internal sensor and a threshold sensor level that is associated with the chosen power output level, the at least one setting being at least one of an oscillator setting of the laser ablation system or an amplifier setting of the laser ablation system, wherein the iteratively (i) receiving and (ii) adjusting in the start-up period dynamically adjust power output of the laser ablation system, and wherein the dynamically adjusting is from the respective power output level, that is less than the chosen power output level, towards the chosen power output level.

13. The method of claim 12, wherein the associated set of configuration settings comprise a voltage level chosen from a plurality of voltage levels for an amplifier and a voltage level chosen from a plurality of voltage levels for an oscillator of the laser ablation system, and wherein adjusting the at least one setting based on the sensor output from the first internal sensor and the threshold sensor level comprises:

determining whether the sensor output from the first internal sensor is less than the threshold sensor level;

responsive to a determination that the sensor output from the first internal sensor is less than the threshold sensor level:
increasing the voltage level for the amplifier, or
decreasing the voltage level for the amplifier and increasing the voltage level for the oscillator;

determining whether the sensor output from the first internal t sensor is greater than the threshold sensor level; and responsive to a determination that the sensor output from the first internal sensor is greater than the threshold sensor level:
decreasing the voltage level for the amplifier, or
increasing the voltage level for the amplifier and decreasing the voltage level for the oscillator.

14. The method of claim 13, wherein determining whether the sensor output from the first internal sensor is less than the threshold sensor level comprises:

determining whether the sensor output from the first internal sensor is less than or equal to a result of the threshold sensor level minus a first range;

determining whether the sensor output from the first internal sensor is less than or equal to a result of the threshold sensor level minus a second range based on a determination that the sensor output of the first internal sensor is less than or equal to the result of the threshold sensor level minus the first range, wherein the second range is greater than the first range.

15. The method of claim 14, wherein determining whether the sensor output from the first internal sensor is greater than the threshold sensor level comprises:

determining whether the sensor output from the first internal sensor is greater than or equal to a result of the threshold sensor level plus the first range;

determining whether the sensor output from the first internal sensor is greater than or equal to a result of the threshold output level plus the second range based on a determination that the sensor output of the first internal sensor is greater than or equal to the result of the threshold sensor level plus the first range.

16. The method of claim 12, wherein the laser ablation system comprises a second internal sensor, the second internal sensor being an internal reflection beam sensor configured to measure an energy of at least a portion of a reflection of the laser beam from a catheter optically coupled to the laser ablation system, and wherein the method further comprises:

receiving a sensor output from the internal reflection beam sensor; and determining whether the sensor output from the internal reflection beam sensor is greater than a threshold reflection beam level or less than the threshold reflection beam level.

17. The method of claim 16, further comprising sending, from the controller, a second control signal to deactivate the laser ablation system based on the determination that the sensor output from the internal reflection beam sensor is greater than the threshold reflection beam level or less than the threshold reflection beam level.

18. The method of claim 16, further comprising generating an indication of an internal malfunction of the laser ablation system based on a determination that the sensor output from the internal reflection beam sensor in greater than the threshold reflection beam level or less than the threshold reflection beam level.

19. The method of claim 12, wherein the power output level is substantially equal to a target power, and wherein the threshold sensor level is associated with a power substantially equal to the target power.

20. A method of controlling a laser ablation system, wherein the laser ablation system includes a laser and a catheter configured to be operatively coupled the laser, comprising:

receiving, at a controller of the laser ablation system, an indication to activate the laser ablation system at a power output level chosen from a plurality of power output levels, the laser ablation system comprising a sensor positioned within the laser and configured to measure an energy of a least a portion of a laser beam generated by the laser before an output of the laser beam by the catheter, wherein each power output level of the plurality of power output levels has an associated set of configuration settings that is preconfigured and that results in the laser ablation system being activated in a start-up period at a respective power output level that is less than the chosen power output level;

sending during the start-up period, from the controller, a control signal to activate the laser ablation system using the associated set of configuration settings for the power output level, wherein using the associated set of configuration settings results in the laser ablation system being activated in the start-up period at the respective power output level that is less than the chosen power output level; and based on activating the laser ablation system, iteratively (i) receiving an output from the first internal sensor and (ii) adjusting at least one setting of the associated set of configuration settings in the start-up period based in-part on the sensor output from the first internal sensor and a threshold sensor level in order to achieve the chosen power output level, the at least one setting being at least one of an oscillator setting of the laser ablation system or an amplifier setting of the laser ablation system, wherein the iteratively (i) receiving and (ii) adjusting in the start-up period dynamically adjust power output of the laser ablation system, and wherein the dynamically adjusting is from the respective power output level, that is less than the chosen power output level, towards the chosen power output level.

\* \* \* \* \*

UNITED STATES PATENT AND TRADEMARK OFFICE
CERTIFICATE OF CORRECTION

PATENT NO. : 12,376,904 B1  
APPLICATION NO. : 17/469839  
DATED : August 5, 2025  
INVENTOR(S) : Stern et al.

Page 1 of 1

It is certified that error appears in the above-identified patent and that said Letters Patent is hereby corrected as shown below:

On the Title Page

Assignee (73): Delete "AngioDynamics, Inc., Latham, NY (US)" and insert -- Eximo Medical LTD., Rehovot (IL) --

Signed and Sealed this  
Sixteenth Day of September, 2025

Coke Morgan Stewart  
*Acting Director of the United States Patent and Trademark Office*